(12) United States Patent
Moshe et al.

(10) Patent No.: US 6,438,261 B1
(45) Date of Patent: Aug. 20, 2002

(54) METHOD OF IN-SITU FOCUS-FUSION MULTI-LAYER SPECTRAL IMAGING AND ANALYSIS OF PARTICULATE SAMPLES

(75) Inventors: Danny S. Moshe, Kiryat Ono; Michael Khazanski, Tel Aviv, both of (IL)

(73) Assignee: Green Vision Systems Ltd., Tel Aviv (IL)

(*) Notice: Subject to any disclaimer, the term of this patent is extended or adjusted under 35 U.S.C. 154(b) by 66 days.

(21) Appl. No.: 09/727,753

(22) Filed: Dec. 4, 2000

Related U.S. Application Data

(63) Continuation-in-part of application No. 09/322,975, filed on Jun. 1, 1999, now abandoned, which is a continuation-in-part of application No. 09/146,361, filed on Sep. 3, 1998, now Pat. No. 6,091,843.

(51) Int. Cl.$^7$ ................................................. G06K 9/00
(52) U.S. Cl. ........................................................ 382/133
(58) Field of Search ................................ 382/128, 133, 382/134, 154, 255; 356/300, 317, 318, 326, 335

(56) References Cited

U.S. PATENT DOCUMENTS

| | | | | |
|---|---|---|---|---|
| 4,631,581 A | * | 12/1986 | Carlsson | 358/93 |
| 5,317,644 A | * | 5/1994 | Kenyon et al. | 382/6 |
| 5,880,830 A | * | 3/1999 | Schechter | 356/318 |
| 6,091,843 A | * | 7/2000 | Horesh et al. | 382/133 |
| 6,215,892 B1 | * | 4/2001 | Douglass et al. | 382/128 |

* cited by examiner

*Primary Examiner*—Andrew W. Johns
(74) *Attorney, Agent, or Firm*—G.E. Ehrlich Ltd.

(57) ABSTRACT

A method for in-situ focus-fusion multi-layer spectral imaging and analysis of depth dependent particulate samples. A unique method of focus-fusion is applied to focused and defocused images acquired from multi-layer spectral imaging of a depth dependent particulate sample, in order to construct fused focused cube spectral image representations of the imaged particles, thereby generating a focused image of essentially each particle in the sample. The method of the present invention features the use of a uniquely defined and calculated focus-fusion factor parameter which combines (1) empirically determined particle physicochemical characteristics relating to (i) particle chemical composition and (ii) particle morphology, with (2) empirically determined particle spectral characteristics relating to (i) image sharpness, (ii) signal-to-noise ratio (S/N), (iii) pixel intensity, (iv) spectral distances, and (v) spectral fingerprints relating to spectral emission patterns of individual particles, and is used in critical steps of image acquisition, target detection, image analysis, and image classification. This uniquely determined parameter enables achievement of high levels of accuracy and precision in imaging and classification of the particulate samples. The method includes collecting and analyzing physicochemical and multi-layer spectral data relating to the particles in the sample, including mapping of three-dimensional positions of particles, particle sizes, and characteristics of particle emission spectra. Scene information, in the form of spectral fingerprints, derived from analysis of focus-fusion of the multi-layer spectral images is further processed using classification procedures in order to extract, on-line, in-situ physicochemical information of the particles, needed for generating a report applicable to monitoring or controlling an industrial process.

38 Claims, 2 Drawing Sheets

---

(1) Providing / preparing particulate sample for spectral imaging and analysis.

(2) Providing a spectroscopic multi-dimensional imaging system.
   (a) Selecting imaging scenario parameters for image acquisition and analysis.
   (b) Performing calibrations using standard samples.

(3) Scanning and imaging the sample at a selected field of view, $FOV_i$.

(4) Acquiring a cube (spectral) plane image of the sample in $FOV_i$ at a selected differential imaging or focusing distance, $\Delta z_{ij}$.

(5) Constructing and analyzing a 'focused' cube (spectral) plane image of the sample from each acquired cube (spectral) plane image, in $FOV_i$ at $\Delta z_{ij}$, from (4).

(6) Repeating (4) - (5) in same $FOV_i$ for selected range of $\Delta z_{ij}$.

(7) Constructing a 'fused' focused cube (spectral) image using high content Blobs and empirical spectral background area parameters, $B_i$.

(8) Constructing additional fused focused cube (spectral) images for other $FOV_i$ by repeating (3) - (7) until sample viewing / imaging range is imaged.

(9) Applying pattern recognition and classification image analysis algorithms to the fused focused cube image data.

(10) Repeating (3) - (9) for each pre-determined time interval, $\Delta t$, and reporting time variation of sample particle characteristics.

(1) Providing / preparing particulate sample for spectral imaging and analysis.

(2) Providing a spectroscopic multi-dimensional imaging system.
    (a) Selecting imaging scenario parameters for image acquisition and analysis.
    (b) Performing calibrations using standard samples.

(3) Scanning and imaging the sample at a selected field of view, $FOV_i$.

(4) Acquiring a cube (spectral) plane image of the sample in $FOV_i$ at a selected differential imaging or focusing distance, $\Delta z_{ij}$.

(5) Constructing and analyzing a 'focused' cube (spectral) plane image of the sample from each acquired cube (spectral) plane image, in $FOV_i$, at $\Delta z_{ij}$, from (4).

(6) Repeating (4) - (5) in same $FOV_i$ for selected range of $\Delta z_{ij}$.

(7) Constructing a 'fused' focused cube (spectral) image using high content Blobs and empirical spectral background area parameters, $B_i$.

(8) Constructing additional fused focused cube (spectral) images for other $FOV_i$ by repeating (3) - (7) until sample viewing / imaging range is imaged.

(9) Applying pattern recognition and classification image analysis algorithms to the fused focused cube image data.

(10) Repeating (3) - (9) for each pre-determined time interval, $\Delta t$, and reporting time variation of sample particle characteristics.

FIG. 1

METHOD OF IN-SITU FOCUS-FUSION MULTI-LAYER SPECTRAL IMAGING AND ANALYSIS OF PARTICULATE SAMPLES

This is a Continuation-in-Part of U.S. patent application Ser. No. 09/322,975, filed Jun. 1, 1999, now abandoned, which is a Continuation-in-Part of U.S. patent application Ser. No. 09/146,361, filed on Sep. 3, 1998, now U.S. Pat. No. 6,091,843, issued Jul. 18, 2000.

FIELD AND BACKGROUND OF THE INVENTION

The present invention relates to methods of imaging and analysis of particles and, in particular, to a method for in-situ focus-fusion multi-layer spectral imaging and analysis of particulate samples.

When a sample featuring, for example, a particle, an aggregate of particles, or a dispersion of particles, has large layer or depth variations relative to changes in the distance from which it is viewed, an image of the sample exhibits a layer dependent or spatially varying degree of sharpness. This is referred to as a defocused image of the sample or scene, where some of the objects of the scene are in focus, while other objects of the scene are out of focus. Defocused images contain information potentially useful for scene analysis. The analysis of scenes from defocused images is of general interest in machine vision applications, for example, in active vision or robot vision where a camera actively explores a scene by continuously changing its position or field of view, relative to scene features. Applying scene analysis to defocused images is highly useful for accurately interpreting and understanding images of pharmaceutical, biomedical, biological, environmental, and microscopy samples, where layer or depth variations of imaged samples of powders, frozen suspensions of powders, biological specimens, air pollution particulates, or other multi-layered particulate samples are typically large compared to imaging distances. Scene analysis of defocused images is of particular applicability to depth dependent particulate samples, where, for instance, one or more layers of bacterial or fungal growth, exhibiting fluorescent emission properties in addition to the fluorescent emission properties of the particles themselves, is present on the particles, and there is a need for separation of imaging and analysis of the bacterial or fungal growth from that of the particles. Additionally, scene analysis is particularly applicable to depth dependent particulate samples of aerosols containing polycyclic aromatic hydrocarbons (PAHs) and other fluorescent particulate contaminants.

In conventional scene analysis using methods and systems for imaging particles, for example, for each scene, there is auto-focusing, where a best focal position is determined for use in analyzing or classifying particle properties. For some scenes, this is possible, and a focused image may be obtained in an automatic manner. Typically, an auto-focus module is coupled with a computer controlled mechanism that automatically changes the focal position, by moving along an axis parallel to the optical axis of the imaging or focusing sensor, thereby enabling identification of a good focal position. For other scenes, a good focal position is not guaranteed to exist and further image processing based on focus-fusion methodology is required.

When a focused image of a spatially varying or depth dependent scene can not be generated by using such electromechanical microscopy means, such that a single focal position can not be identified, a focused representation of the scene can be constructed by combining or fusing several defocused images of the same scene. This process is referred to as focus-fusion imaging, and the resulting image of such processing is referred to as a focus-fusion image. Defocused images, for example, those acquired during auto-focusing, are fused together such that each target in a given scene is in correct focus. Scene targets are detected by analyzing either the focused image, if it exists, or the focus-fusion image.

A current technique of imaging particles is based on spectral imaging. In spectral imaging, a particulate sample is affected in a way, for example, excitation by incident ultraviolet light upon the sample, which causes the sample to emit light featuring an emission spectra. Emitted light is recorded by an instrument such as a scanning interferometer that generates a set of interferogram images, which in turn are used to produce a spectral image, also referred to as a cube image, of the sample. Each cube (spectral) image is a three dimensional data set of voxels (volume of pixels) in which two dimensions are spatial coordinates or position, (x, y), in the sample and the third dimension is the wavelength, ($\lambda$), of the imaged (emitted) light of the sample, such that coordinates of each voxel in a spectral image or cube image may be represented as (x, y, $\lambda$). Any particular wavelength, ($\lambda$), of imaged light of the sample is associated with a set of cube images or spectral fingerprints of the sample in two dimensions, for example, along the x and y directions, whereby voxels having that value of wavelength constitute the pixels of a monochromatic image of the sample at that wavelength. Each cube image, featuring a range of wavelengths of imaged light of the sample is analyzed to produce a two dimensional map of the chemical composition, or of some other physicochemical property of the sample, for example, particle size distribution.

An example of a method and system for real-time, on-line chemical analysis of particulate samples, for example, polycyclic aromatic hydrocarbon (PAH) particles in aerosols, in which the PAH sample is excited to emit light, for example fluorescence, is that of U.S. Pat. No. 5,880,830, issued to Schechter, and manufactured by GreenVision Systems Ltd. of Tel Aviv, Israel, and is incorporated by reference for all purposes as if fully set forth herein. In the disclosed method, spectral imaging techniques are implemented to acquire an image and analyze the properties of fixed position PAH particles. As part of this method, air is sampled by means of a high volume pump sucking a large volume of air featuring aerosol contaminated with PAH particles onto a substrate, followed by on-line imaging and scene analysis of the stationary particles.

A method of calibration and real-time analysis of particles is described in U.S. Pat. No. 6,091,843, to Moshe et al., and is incorporated by reference for all purposes as if fully set forth herein. The method described, is based on using essentially the same system of U.S. Pat. No. 5,880,830, for acquiring spectral images of static particles on a filter. Targets are identified in static particle images and are classified according to morphology type and spectrum type. Each target is assigned a value of an extensive property. A descriptor vector is formed, where each element of the descriptor vector is the sum of the extensive property values for one target class. The descriptor vector is transformed, for example, to a vector of mass concentrations of chemical species of interest, or of number concentrations of biological species of interest, using a relationship determined in the calibration procedure. In the calibration procedure, spectral images of calibration samples of static particles having known composition are acquired, and empirical morphology types and spectrum types are inferred from the spectral images. Targets are identified in the calibration spectral images, classified according to morphology type and spectrum type, and assigned values of an extensive property. For each calibration sample, a calibration descriptor vector and a calibration concentration vector is formed. A collective relationship between the calibration descriptor vectors and the calibration concentration vectors is found using chemometric methods.

In the method of U.S. Pat. No. 6,091,843, standard spectra are determined empirically in the calibration procedure. In such analytical procedures, empirical calibration is quite important for leading to highly accurate results based on image analysis and classification, because spectra of adsorbed chemical species in general, and, of PAHs in particular, are known to be altered by the surfaces on which they are adsorbed, and by the presence of contaminants during sample preparation and image acquisition. Moreover, in the described method, the relationship between the descriptor vector and the concentration vector accounts explicitly and simultaneously for both morphologies and empirically determined spectra. This is particularly important in cases where fluorescence spectra of crystal particles are known to depend on crystal morphology, in general, and crystal size, in particular.

Spectral imaging of spatially varying, depth dependent, or multi-layered samples of particles is not described in the above referenced methods and systems. Imaging and image analysis of a random single two-dimensional layer of a sample including particles are ordinarily straightforward. However, multi-layer imaging and image analysis of depth dependent particulate samples, for example, multi-layered dry particles, or particles in a frozen or immobilized suspension, are substantially more complex, for the reasons stated above. More often than not, images obtained of such particulate samples are defocused, and require special image processing techniques, such as focus-fusion, for obtaining useful information about the samples. Nevertheless, there are instances where it is necessary to obtain property and classification information of depth dependent particulate samples, in-situ, for example, as part of sampling an industrial process. In principle, a sample of dispersed or multi-layered particles is amenable to three-dimensional imaging and scene analysis. In practice, however, for depth dependent samples of particles, spectral imaging as presently practiced would involve tedious methodologies and system manipulations, making acquisition of high resolution images impossible or at best impracticable.

Scene analysis by applying focus-fusion methodology to defocused images acquired by multi-layer spectral imaging of depth dependent particulate samples would be quite useful for detecting and classifying in-situ physicochemical information of the particles, such as particle size distribution, morphological features, including structure, form, and shape characteristics, and chemical composition, which ideally involve multi-layer three-dimensional image analysis. For fusing defocused images, current focus-fusion procedures and algorithms typically involve information and parameters relating only to the extent to which acquired images are either focused or defocused, without inclusion of additional information and parameters specifically relating to particular properties and characteristics of the imaged object or sample, and relating to the information and parameters of the spectral imaging process. Characteristic sample physicochemical and spectral information and parameters can be quite relevant to imaging particulate samples, and ought to be included in a method of focus-fusion of acquired images of such samples. This is especially the case for images of particulate samples featuring layer dependent or spatially varying degree of sharpness. There is thus a recognized need for, and it would be highly advantageous to have, a method for in-situ focus-fusion multi-layer spectral imaging and analysis of depth dependent particulate samples.

SUMMARY OF THE INVENTION

The present invention relates to a method for in-situ focus-fusion multi-layer spectral imaging and analysis of depth dependent particulate samples. A unique method of focus-fusion is applied to focused and defocused images acquired from multi-layer spectral imaging of a depth dependent particulate sample, in order to construct focused fused cube (spectral) image representations of the imaged particles, thereby generating a focused image of essentially each particle in the sample. The method of the present invention introduces the use of a uniquely defined and calculated focus-fusion factor parameter, $F_f$, which combines (1) empirically determined particle physicochemical information and parameters relating to (i) particle chemical composition and associated chemistry, and relating to (ii) particle morphology such as particle size and shape, with (2) empirically determined particle spectral information and parameters such as (i) pixel intensity, (ii) signal-to-noise ratio (S/N), (iii) image sharpness, (iv) spectral distances, and (v) spectral fingerprints relating to spectral emission patterns of individual particles. The focus-fusion factor parameter, $F_f$, is used in critical steps of image detection, image analysis, and in algorithms for classification of particle characteristics. This uniquely determined parameter enables achievement of high levels of accuracy and precision in detection and classification of the sample, in general, and of the featured particles, in particular.

The method of the present invention includes collecting and analyzing physicochemical and multi-layer spectral data relating to the particles in the sample, including mapping of three-dimensional positions of particles, particle sizes, and characteristics of particle emission spectra. Scene information, in the form of spectral fingerprints, used in the analysis of focus-fusion of the multi-layer spectral images is further processed in order to generate relevant in-situ physicochemical information of the particles, such as particle size distribution, morphological features, including structure, form, and shape characteristics, and chemical composition. The focus-fusion multi-layer spectral image analysis includes a sophisticated classification procedure for extracting, on-line, useful information relating to particle properties and characteristics needed for generating a report applicable to monitoring or controlling an industrial process.

The method of the present invention enables multi-layer spectral imaging, multi-layer scene analysis, and multi-layer physicochemical characterization of particulate samples featuring depth dependency, which until now has not been described in the prior art of spectral imaging technology or of focus-fusion technology. Implementing the present invention is highly useful for accurately interpreting and understanding images of pharmaceutical, biomedical, biological, environmental, and microscopy samples, where layer or depth variations of imaged samples of powders, frozen suspensions of powders, biological specimens, air pollution particulates, or other multi-layered particulate samples are typically large compared to differential imaging distances.

In the pharmaceutical industry, applying the method for in-situ multi-layer focus-fusion spectral imaging and analysis of particulate samples is of particular applicability to depth dependent particulate samples of powders, where, for instance, one or more layers of bacterial or fungal growth, exhibiting fluorescent emission properties in addition to the fluorescent emission properties of the particles themselves, is present on the particles, and there is a need for separation of imaging and analysis of the bacterial or fungal growth from that of the particles. Additionally, the present invention is very well suited for analyzing defocused images of multi-component particulate samples of medicines, for example, medicines containing both active and inactive ingredients, whereby there is distinguishing and characterizing physicochemical properties and features of the active and inactive ingredients. In the environmental field of analyzing, monitoring, and controlling air pollution, the present method for focus-fusion spectral imaging scene analysis is particularly applicable to depth dependent particulate samples, such as airborne aerosols containing polycyclic aromatic hydrocarbons (PAHs) and other fluorescent particulate contaminants.

According to the present invention, there is provided a method for multi-layer imaging and analyzing a sample featuring particles, imaged particles exhibiting a spatially varying degree of sharpness, the method comprising the steps of: (a) providing a spectroscopic imaging system, including a sample holder movable by a three dimensional translation stage; (b) selecting and defining imaging scenario parameters for acquiring and analyzing spectral images of the sample, the imaging scenario parameters are particle physicochemical characteristics relating to particle chemical composition and particle morphology, and, particle spectral characteristics relating to pixel intensity, signal-to-noise, image sharpness, spectral distances, and spectral fingerprints relating to spectral emission patterns of individual particles; (c) adjusting and setting the spectroscopic imaging system for imaging at a selected field of view, $FOV_i$, having central (x, y) position coordinates; (d) acquiring a cube (spectral) plane image of the sample in the selected field of view at a selected differential imaging/focusing distance, $\Delta z_{ij}$, by focusing the imaging system in z-direction until receiving a sharp gray level image of the sample; (e) constructing and analyzing a focused cube (spectral) plane image of the sample for an i-th field of view, $FOV_i$, at a j-th differential imaging/focusing distance, $\Delta z_{ij}$, from the cube (spectral) plane image of the sample acquired in the step (d), whereby the constructing and analyzing are based on using a combination of the selected and the defined particle physicochemical and particle spectral imaging scenario parameters of the step (b); (f) repeating the step (d) and the step (e) in the same field of view, $FOV_i$, for a selected range of imaging distance defined along the z-direction between the sample light illumination source of the imaging system, acquiring a plurality of the cube (spectral) plane images of the sample in a corresponding plurality of the selected i-th fields of view, $FOV_i$, wherein for each the i-th field of view, $FOV_i$, there is imaging at a plurality of the selected j-th differential imaging or focusing distances, $\Delta z_{ij}$; (g) constructing a fused focused cube (spectral) image from the plurality of the focused cube (spectral) plane images and empirically determined spectral background parameters, $B_i$, obtained from the plurality of the focused cube (spectral) plane images; (h) acquiring and constructing additional fused focused cube (spectral) images of the sample in other fields of view, $FOV_i$, for a plurality of the differential imaging/focusing distances, $\Delta z_{ij}$, by repeating the step (c) through the step (g), until selected sample viewing/imaging range is imaged; (i) applying at least one image analysis algorithm to data of the plurality of the fused focused cube (spectral) images, for identifying spectral fingerprints relating to physicochemical characterization of the sample; and (j) repeating the step (c) through the step (i) over a period of time spanning a multiple of a predetermined time interval, $\Delta t$, whereby following each predetermined time interval, $\Delta t$, generating a statistical analysis report describing time variation of physicochemical and spectral imaging characteristics of the particulate sample.

Two types of 'spectral distances' are used in the description of the method for focus-fusion multi-layer spectral imaging of the present invention. The first type of spectral distance is the Blob neighborhood spectral distance parameter, $D_s$, defined as the physical, geometrical distance encompassing a number of selected neighboring Blobs in the same Blob neighborhood as a particularly identified sharp or focused $Blob_b$, referred to as $Blob_s$, for s=1 to any number, S, of sharp or focused $Blob_s$, each having central gravity position coordinates $(x_s, y_s)$. In a Blob neighborhood, the sharp or focused $Blob_s$, and the selected neighboring or neighborhood $Blobs_b$ are considered suitable for including in the process of constructing focused cube (spectral) plane images and in constructing 'fused' focused cube (spectral) images of a sample. Blob neighborhood spectral distance parameter, $D_s$, is determined according to criteria specific to a particular application, for example, in-situ, while the detecting, imaging, and analysis of Blobs is in progress, and is a function of particle spectral information and parameters, such as pixel intensity, signal-to-noise ratio (S/N) of imaging or spectral signals corresponding to Blob and non-Blob pixels, image sharpness, and spectral fingerprints relating to spectral emission patterns of individual particles.

The second type of spectral distance is the inter-Blob spectral distance, $\Delta d_{bs}$, defined as the physical geometrical distance between an identified Blob, $Blob_b$, having position coordinates $(x_b, y_b)$, and a sharp or focused Blob, $Blob_s$, having position coordinates $(x_s, y_s)$, both located in the same i-th field of view, $FOV_i$, at the same j-th differential imaging or focusing distance, $\Delta z_{ij}$.

In the present invention, there is calculating a focus-fusion factor parameter, $F_b$, from a set of calculated physicochemical and spectral parameters for each identified Blob, $Blob_b$, in the i-th field of view, $FOV_i$, at the j-th differential imaging or focusing distance, $\Delta z_{ij}$, of a cube (spectral) plane image of a sample, by using a formula based on applying fuzzy logic analysis:

$$F_b = \text{fuzzy logic function [(physicochemical parameters of } Blob_b),\\ \text{(spectral parameters of } Blob_b)],$$

where the physicochemical parameters of $Blob_b$ relate to particle chemistry and particle morphology, and the spectral parameters of $Blob_b$ relate to spectral fingerprints featured in spectral emission patterns of individual particles of the sample.

BRIEF DESCRIPTION OF THE DRAWINGS

The invention is herein described, by way of example only, with reference to the accompanying drawings, wherein:

FIG. 1 is a flow diagram of an exemplary preferred embodiment of the method for in-situ focus-fusion multi-layer spectral imaging and analysis of particulate samples, in accordance with the present invention.

DESCRIPTION OF THE PREFERRED EMBODIMENTS

Figure 2:
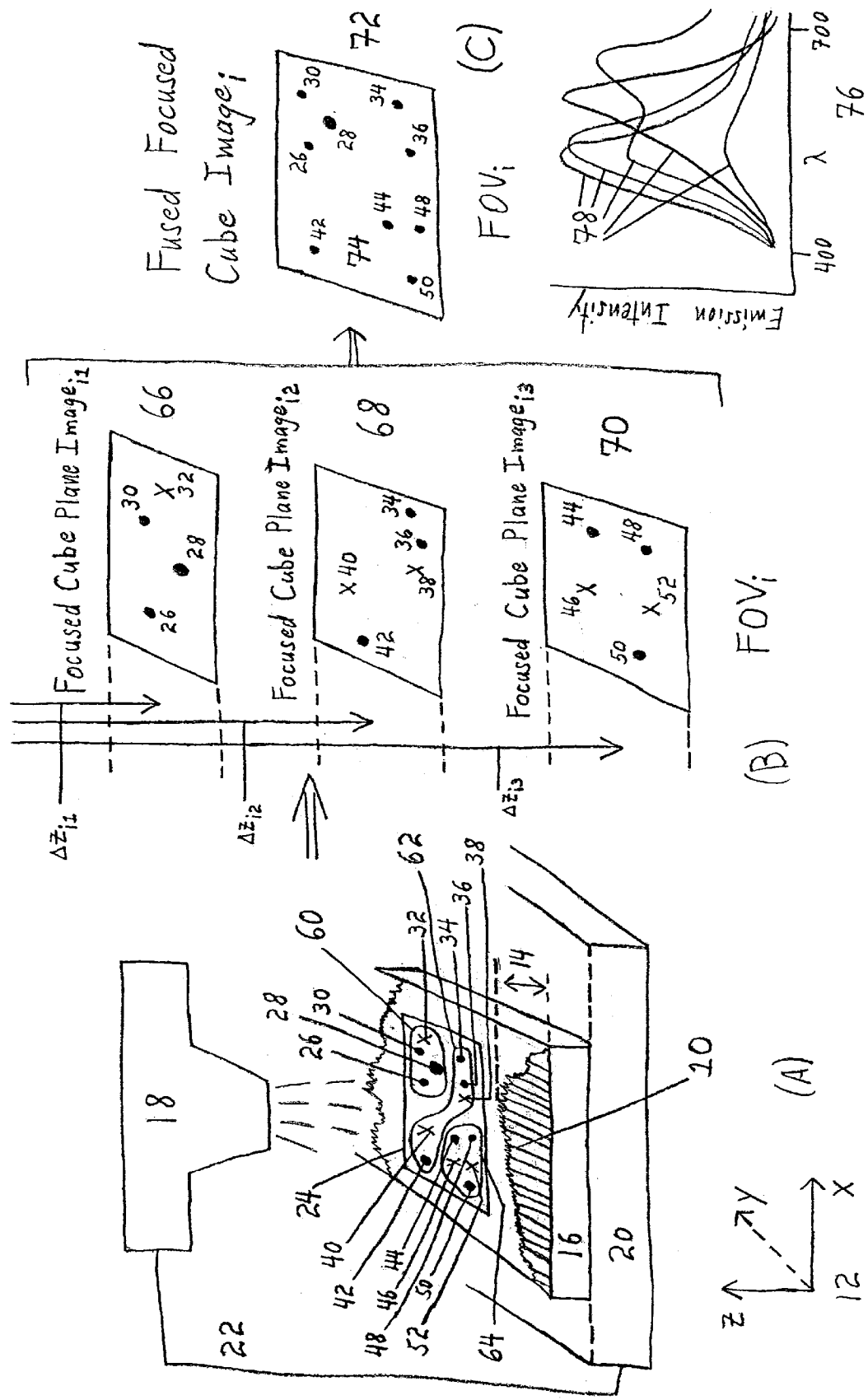
FIGS. 2(A–C) is a schematic diagram illustrating implementation of selected steps of the preferred embodiment of the method for in-situ focus-fusion multi-layer spectral imaging and analysis of particulate samples, in accordance with the present invention.

The present invention is of a method for in-situ focus-fusion multi-layer spectral imaging and analysis of particulate samples. Steps and implementation of the method according to the present invention are better understood with reference to the drawings and the accompanying description. It is to be noted that illustrations of the present invention shown here are for illustrative purposes only and are not meant to be limiting.

Referring now to the drawings, FIG. 1 is a flow diagram of an exemplary preferred embodiment of the method for in-situ focus-fusion multi-layer spectral imaging and analysis of particulate samples. In FIG. 1, each generally applicable, principle step of the method of the present invention is numbered and enclosed inside a frame. Sub-steps representing further of an indicated principle step of the method are indicated by a letter in parentheses. FIG. 2 is a schematic diagram illustrating implementation of selected steps of the preferred embodiment of the method for in-situ focus-fusion multi-layer spectral imaging and analysis of particulate samples. Referenced items shown in FIG. 2 relevant to understanding the method of FIG. 1 are referred to and described in the description of FIG. 1.

In Step (1), a sample 10 (FIG. 2(A)) featuring particles is provided, and prepared for multi-layer spectral imaging and analysis. Sample 10, could be, for example, a pure powder or a powder mixture, a frozen suspension of a powder, a biological specimen, or some other multi-layered particulate sample, and features a three dimensional topography using coordinate system 12 as a reference, whereby there are layer or depth variations in the z-direction along sample height 14 which are relatively large compared to differential imaging distances in the z-direction between sample 10 and imaging device 18. Sample 10 is placed on a sample holder 16, where sample 10 and sample holder 16 are either exposed to ambient conditions, for example, a powdered sample resting on a glass slide without controlled environmental containment, or, are contained in a controlled environment, for example, a frozen suspension maintained at or below the freezing point temperature of such a frozen suspension.

In Step (2), a spectroscopic imaging system 18, including a three dimensional translation stage 20 is provided. Examples of a spectroscopic imaging system 18, including peripheral apparatus, and control/data links, appropriate for implementation of the method of the present invention are fully described in U.S. Pat. No. 5,880,830, issued to Schechter, and references cited therein, which are incorporated by reference for all purposes as if fully set forth herein. Spectroscopic imaging system 18 includes, among other components, an ultraviolet light illumination source, an optical system, a spectroscopic imaging device, a CCD camera having suitable sensitivity and dynamic range, a central control system, and control/data links. In spectroscopic imaging system 18, the light source homogeneously illuminates particles of sample 10, either by combined operation with the optical system, or directly without combined operation of the optical system. The control system is based on a personal computer, and includes a frame grabber for acquiring images from the CCD camera, as well as other hardware interface boards for controlling translation stage 20 and the other components of spectroscopic imaging system 18. The software of the control system includes a database of empirically determined morphology types and spectrum types and codes for implementing the image processing and quantification algorithms described below.

Spectroscopic imaging system 18 also includes a three dimensional translation stage 20 used for synchronized electronic three dimensional movement and positioning of sample holder 16, and therefore, sample 10. Translation stage 20 is in electronic communication with spectroscopic imaging system control devices via control/data links 22. Operating translation stage 20 enables spectroscopic imaging system 18 to automatically focus and image sample 10 in a plurality of pre-selected fields of view, $FOV_i$, for i=1 to any number, I, of fields of view, for example, field of view 24, and along a plurality of pre-selected focal planes or focal distances in the z-direction differing by a differential imaging or focusing distance, $\Delta z_{ij}$, for potentially imaging entire sample 10. Accordingly, for each i-th field of view, $FOV_i$, for example, field of view 24, sample 10 is imaged for at least two, preferably, a plurality of, differential imaging or focusing distances, $\Delta z_{ij}$, by using translation stage 20 for imaging different depths or planes along sample height 14, whereby $\Delta z_{ij}$ corresponds to the j-th differential imaging or focusing distance in i-th field of view, $FOV_i$, of sample 10, for j=1 to any number, J, of differential imaging or focusing distances.

In sub-step (a) of Step (2), there is selecting and defining imaging scenario parameters to be used for image acquisition and analysis. These include (1) empirically determined particle physicochemical information and parameters relating to (i) particle chemical composition and associated chemistry, and relating to (ii) particle morphology such as particle size and shape, and (2) empirically determined particle spectral information and parameters such as (i) pixel intensity, (ii) signal-to-noise ratio (S/N), (iii) image sharpness, (iv) spectral distances, and (v) spectral fingerprints relating to spectral emission patterns of individual particles.

Most of the above list of imaging scenario parameters are well known and used by persons skilled in the technologies of spectral imaging and focus-fusion imaging, and need not be defined herein for properly understanding the present invention. Terms relevant to properly understanding usage of the imaging scenario parameters in the present invention are defined herein. In particular, the second category of imaging scenario parameters, (2) the empirically determined particle spectral information and parameters such as (i) pixel intensity, (ii) signal-to-noise ratio (S/N), (iii) image sharpness, (iv) spectral distances, and (v) spectral fingerprints relating to spectral emission of individual particles.

One of the main objectives of spectral imaging sample 10, is to obtain data and information which can be used for applying one or more classification algorithms for identifying and characterizing features of practical interest relating to particulate sample 10. An effective way of performing spectral imaging and analyzing the spectral data and information of sample 10 is to use the term 'Blob' for referring to a detected target in a gray level image of sample 10. In the present invention, a Blob, hereinafter, also generally referred to as a b-th Blob, $Blob_b$, for b=1 to any number, B, of $Blobs_b$, is made up of a cube (spectral) set of groups or clusters of individual pixels in a gray level image representation of sample 10, where each pixel has a location or position coordinates, (x, y), and an energy level or intensity, I(p), in the gray level image of sample 10. Furthermore, a Blob is defined such that (1) a sufficiently high fraction of all the pixels in the group or cluster of pixels constituting the Blob consists of pixels each having an energy level or intensity, I(p), above a pre-determined threshold pixel energy level or intensity, $I_T(p)$, and such that (2) the signal-to-noise ratio, (S/N), associated with the signal corresponding to the summed or integrated intensities of the pixels of the $Blob_b$ must be sufficiently high.

The gray level image representation of each $Blob_b$ is obtained by summing or integrating the set of pixel energy levels or intensities, I(p), associated with the three-dimensional voxels having position coordinates, (x, y), for a given spectral wavelength range of the cube (spectral) image of each $Blob_b$. Specifically, for each $Blob_b$ featuring voxels having the same position coordinates, (x, y), the set of pixel intensities associated with a plurality of emission spectra in the wavelength range $\lambda_L, \ldots, \lambda_U$, where $\lambda_L$ and $\lambda_U$ are measured values of lower and upper wavelengths of the light emitted by particulate sample 10, respectively, are summed or integrated, to give the summed or integrated gray level image of each $Blob_b$.

The central gravity point or central gravity position of each $Blob_b$ is determined from the pixel of the cube (spectral) set of groups or clusters of pixels, making up $Blob_b$, which has the highest energy level or intensity, I(p), compared to the energy levels or intensities of the eight closest pixels neighboring that highest intensity pixel. Hereinafter, for simplicity, the central gravity point or central gravity position of each $Blob_b$ is referred to as the position or position coordinates $(x_b, y_b)$ of that $Blob_b$ in the gray level image of sample 10. Consistent with this definition of a Blob, is that, in principle, a Blob is an image representation of any portion or of an entirety of particulate sample 10. In ordinary practice, it is desired that detection of a Blob be indicative of a sharp or focused image of at least part of a single particle of sample 10. One of the primary tasks of the unique image acquisition and analysis method of the present invention is to distinguish meaningful or high content Blobs featuring useful information relating to particle characteristics from Blobs featuring non-relevant information, such as contamination of sample particles or contamination of the imaging system due to less than ideal experimental conditions or due to experimental error.

Two types of 'spectral distances' are used in the description of the method for focus-fusion multi-layer spectral imaging of the present invention. The first type of spectral distance is the Blob neighborhood spectral distance parameter, $D_s$, defined as the physical geometrical distance encompassing a number of selected neighboring Blobs in the same Blob neighborhood as a particularly identified sharp or focused $Blob_b$, hereinafter, referred to as $Blob_s$, for s=1 to any number, S, of sharp or focused $Blob_s$, each having central gravity position coordinates $(x_s, y_s)$. In a Blob neighborhood, the sharp or focused $Blob_s$, and the selected neighboring or neighborhood $Blobs_b$ are considered suitable for including in the process of constructing focused cube (spectral) plane images and in constructing 'fused' focused cube (spectral) images of sample 10. Blob neighborhood spectral distance parameter, $D_s$, is determined according to criteria specific to a particular application, for example, in-situ, while the detecting, imaging, and analysis of Blobs is in progress, and is a function of particle spectral information and parameters, such as pixel intensity, signal-to-noise ratio (S/N) imaging or spectral signals corresponding to Blob and non-Blob pixels, image sharpness, and spectral fingerprints relating to spectral emission patterns of individual particles.

The second type of spectral distance is the inter-Blob spectral distance, $\Delta d_{bs}$, defined as the physical geometrical distance between an identified Blob, $Blob_b$, having position coordinates $(x_b, y_b)$, and a sharp or focused Blob, $Blob_s$, having position coordinates $(x_s, y_s)$, both located in the same i-th field of view, $FOV_i$, at the same j-th differential imaging or focusing distance, $\Delta z_{ij}$.

In the present invention, 'image sharpness' refers to the extent or degree of sharpness or focus of a gray level image of sample 10, in general, and to the extent or degree of sharpness or focus of local regions of sample 10, in particular, such as extent or degree of sharpness or focus of an entire particle or part of a particle of sample 10. Accordingly, the spectral parameter of image sharpness is extendable to Blobs, defined above, whereby there is a measure of the extent or degree of sharpness or focus of each $Blob_b$ in a gray level image of sample 10. In particular, according to the above description, a Blob neighborhood is established by identifying a sharpest or most focused Blob, $Blob_s$, having position coordinates $(x_s, y_s)$. During spectral imaging of sample 10, in a given gray level image of sample 10, there may be identified only one sharp or focused Blob, $Blob_s$, or, there may be identified a plurality of any number, S, of sharp or focused Blobs, for example, a first sharpest or most focused Blob, $Blob_1$, a second sharpest or most focused Blob, $Blob_2$, a third sharpest or most focused Blob, $Blob_3$, and so on until identifying the last sharpest or most focused Blob, $Blob_S$, of all the remaining detected $Blobs_b$, according to the above specific criteria for identifying a sharp or focused Blob, $Blob_s$.

Having described the imaging scenario parameters which are used in the image acquisition and analysis, it is noteworthy to emphasis an important aspect of the novelty of the method of the present invention. A Blob neighborhood is established, and therefore, values of the Blob neighborhood spectral distance parameter, $D_s$, and the inter-Blob spectral distance, $\Delta d_{bs}$, are determined by using criteria involving the above listed particle spectral parameters, (i) pixel intensity, (ii) signal-to-noise ratio (S/N), (iii) image sharpness, and (v) spectral fingerprints.

Specifically, only a Blob, $Blob_s$, being sufficiently sharp or focused is used for establishing a Blob neighborhood. Accordingly, first, with respect to (i) pixel intensity, in order for an imaged feature or target of sample 10 to be identified as an ordinary Blob, $Blob_b$, the $Blob_b$ must contain a sufficiently high fraction of all the pixels in the group or cluster of pixels constituting $Blob_b$ consisting of pixels each having an energy level or intensity, I(p), above a pre-determined threshold pixel energy level or intensity, $I_T(p)$. Second, with respect to (ii) signal-to-noise ratio (S/N), the signal-to-noise ratio, (S/N), associated with the imaging signal or spectrum corresponding to the summed or integrated intensities of the pixels of the $Blob_b$ must be sufficiently high. Third, with respect to (iii) image sharpness, having satisfied the previous two criteria, in order for an ordinary Blob, $Blob_b$, to be identified as a sharp or focused Blob, $Blob_s$, used as a reference Blob for establishing a Blob neighborhood, the $Blob_b$ must be sufficiently sharp or focused in the particular gray level image of sample 10. Fourth, with respect to (v) spectral fingerprints, relating to spectral emission patterns of individual particles.

In sub-step (b) of Step (2), there is performing calibrations on standard samples with known physicochemical and spectral imaging characteristics relating to, or expected to be observed in, sample 10, according to methodology described in U.S. Pat. No. 6,091,843, cited above, which is incorporated by reference for all purposes as if fully set forth herein. Results of the calibrations are used as part of image analysis of sample 10.

From the calibrations, targets are identified in static particle images of sample 10 and are classified according to physicochemical (morphology) type and spectrum type. Each target is assigned a value of an extensive property. A descriptor vector is formed, where each element of the descriptor vector is the sum of the extensive property values for one target class. The descriptor vector is transformed, for example, to a vector of mass concentrations of chemical species of interest, or of number concentrations of biological species of interest, relating to a given sample 10, using a relationship determined in the calibration procedure. In the calibration procedure, spectral images of calibration samples of static particles of sample 10 having known chemical composition and particle morphology are acquired, and empirical morphology types and spectrum types are inferred from the spectral images. Targets are identified in the calibration spectral images, classified according to morphology type and spectrum type, and assigned values of an extensive property. For each calibration sample, a calibration descriptor vector and a calibration concentration vector is formed. A collective relationship between the calibration descriptor vectors and the calibration concentration vectors is found using chemometric methods.

In Step (3), there is scanning sample 10 by adjusting and setting spectroscopic imaging system 18 for spectral imaging at a selected field of view, $FOV_i$, for example, field of view 24, over sample 10, having central (x, y) coordinates relative to translation stage 20, by moving translation stage 20 increments of $\Delta x$ and $\Delta y$.

In Step (4), there is acquiring a cube (spectral) plane image of sample 10, in the selected i-th field of view, $FOV_i$, at a selected j-th differential imaging or focusing distance, $\Delta z_{ij}$, by focusing imaging system 18 by moving translation stage 20 in the z-direction an increment $\Delta z$, until receiving a sharp gray level image of sample 10. This corresponds to adjusting and setting imaging system 18 for spectral imaging sample 10 in the x-y plane of the i-th field of view, $FOV_i$, for a selected imaging distance defined along the z-axis between sample 10 and the light illumination source of imaging system 18. This step of acquiring spectral data and information is needed for constructing a single 'focused' cube (spectral) plane image of sample 10, as described below in Step (5).

Each succeeding performance of Step (4), for the same field of view, $FOV_i$, selected according to Step (3), corresponds to adjusting and setting spectroscopic imaging system 18 for spectral imaging at another selected j-th differential imaging or focusing distance, $\Delta z_{ij}$, in the i-th field of view, $FOV_i$, of sample 10, as described below in Step (6). Including Step (4) in the method of the present invention is essential for constructing a plurality of focused cube (spectral) plane images of sample 10. From each plurality of focused cube (spectral) plane images obtained for each i-th field of view, $FOV_i$, of sample 10, there is constructed a fused focused cube (spectral) image, as described below in Step (7).

Each cube (spectral) plane image acquired in the i-th field of view, $FOV_i$, at the j-th differential imaging or focusing distance, $\Delta z_{ij}$, features pixels, where the pixels have at least one common visual property, and each pixel has a location. Acquired cube (spectral) plane images are digitized and analyzed by standard methods for analyzing cube (spectral) images. Each cube (spectral) plane image is a three dimensional data set of voxels (volume of pixels) in which two dimensions are spatial coordinates or position, (x, y), in sample 10 and the third dimension is the wavelength, ($\lambda$), of the imaged (emitted) light of sample 10, such that coordinates of each voxel in each spectral image or cube image may be represented as (x, y, $\lambda$). Any particular wavelength, ($\lambda$), of imaged light of sample 10 is associated with a set of cube images or spectral fingerprints of sample 10 in two dimensions, for example, along the x and y directions, whereby voxels having that value of wavelength constitute the pixels of a monochromatic image of sample 10 at that wavelength. Each cube (spectral) plane image, featuring a range of wavelengths of imaged light of sample 10 is analyzed to produce a two dimensional map of the chemical composition, or of some other physicochemical property of sample 10, for example, particle size distribution.

In Step (5), there is constructing and analyzing a 'focused' cube (spectral) plane image of sample 10, for the i-th field of view, $FOV_i$, at the j-th differential imaging or focusing distance, $\Delta z_{ij}$, from the cube (spectral) plane image of sample 10 acquired in Step (4). Hereinafter, a focused cube (spectral) plane image of sample 10 is also referred to as focused cube plane image$_{ij}$, corresponding to a focused cube (spectral) image constructed from a cube (spectral) plane image acquired in the i-th field of view, $FOV_i$, at the j-th differential imaging or focusing distance, $\Delta z_{ij}$.

In sub-step (a), of Step (5), there is identifying Blobs, if present, in the cube (spectral) plane image of sample 10, acquired in Step (4). Each Blob$_b$ is identified according to the criteria of having a sufficiently high fraction of all the pixels in the cube (spectral) set of groups or clusters of pixels constituting Blob$_b$ consisting of pixels each having an energy level or intensity, I(p), above a pre-determined threshold pixel energy level or intensity, $I_T(p)$, and the signal-to-noise ratio, (S/N), associated with the gray level imaging signal or spectrum corresponding to the summed or integrated intensities of the pixels of the Blob$_b$ must be sufficiently high.

For illustrative purposes only, and not being limited to quantities or numbers, the following exemplary description is provided herein. In FIG. 2(A), in exemplary i-th field of view, $FOV_i$, 24, over sample 10, there is shown a plurality of fourteen Blobs$_b$, for b=1 to 14, drawn as solid circles and 'x's, and referred to as Blob$_1$ 26, Blob$_2$ 28, Blob$_3$ 30, Blob$_4$ 32, Blob$_5$ 34, Blob$_6$ 36, Blob$_7$ 38, Blob$_8$ 40, Blob$_9$ 42, Blob$_{10}$ 44, Blob$_{11}$ 46, Blob$_{12}$ 48, Blob$_{13}$ 50, and Blob$_{14}$ 52, having position coordinates $(x_1, y_1)$, $(x_2, y_2)$, $(x_3, y_3)$, $(x_4, y_4)$, $(x_5, y_5)$, $(x_6, y_6)$, $(x_7, y_7)$, $(x_8, y_8)$, $(x_9, y_9)$, $(x_{10}, y_{10})$, $(x_{11}, y_{11})$, $(x_{12}, y_{12})$, $(x_{13}, y_{13})$, and $(x_{14}, y_{14})$, respectively. In FIG. 2(A), these fourteen exemplary Blobs$_b$ are shown segregated into three separated Blob regions or Blob neighborhoods, referred to as first Blob neighborhood 60, second Blob neighborhood 62, and third Blob neighborhood 64.

For the purpose of description, each Blob neighborhood 60, 62, and 64, corresponds to a 'portion' of a different single cube (spectral) plane image acquired for the 'same' i-th field of view, $FOV_i$, 24, but, at a different j-th differential imaging or focusing distance, $\Delta z_{ij}$. In other words, each Blob neighborhood 60, 62, and 64, is actually part of a different single cube (spectral) plane image acquired by focusing spectroscopic imaging system 18 by moving translation stage 20 for obtaining a different total imaging length in the z-direction between sample 10 and imaging device 18, where the total imaging lengths differ by the differential imaging or focusing distance, $\Delta z_{ij}$. Accordingly, each Blob neighborhood 60, 62, and 64, corresponds to a 'portion' of a different single cube (spectral) plane image acquired for the same i-th field of view, $FOV_i$, 24, at differential imaging or focusing distances, $\Delta z_{ij}$, for j=1 to 3, or, at $\Delta z_{i1}$, $\Delta z_{i2}$, and $\Delta z_{i3}$, respectively.

Additionally, for the purpose of description, in each Blob neighborhood 60, 62, and 64, there is drawn only Blobs$_b$ which are identified in the image of sample 10 according to the previously described criteria for being a Blob$_b$. During actual imaging conditions, a given acquired cube (spectral) plane image may include a number of Blobs selected from the group consisting of no identifiable $Blob_b$, a single identifiable $Blob_b$, for b=1, and, a plurality of identifiable $Blobs_b$, for b=2 to any number, B, of Blobs, where each $Blob_b$ is made up of a group or cluster of individual pixels, where each pixel has a location or position coordinates, (x, y), and an energy level or intensity, I(p), in the gray level image of sample 10. Furthermore, during actual imaging conditions, a given acquired cube (spectral) plane image may also include non-Blob spectral features and/or artifacts (not shown in FIG. 2(A)) not satisfying the above described criteria for being identified as a Blob, $Blob_b$, arising from such effects due to contamination of sample particles or contamination of the imaging system due to less than ideal experimental conditions or due to experimental error.

In sub-step (b), of Step (5), there is grouping a number of neighboring identified Blobs, $Blobs_b$, from all identified Blobs, $Blobs_b$, into one or more Blob neighborhoods, for the cube (spectral) plane image of sample 10 acquired for the i-th field of view, $FOV_i$, at the j-th differential imaging or focusing distance, $\Delta z_{ij}$, from Step (4).

A Blob neighborhood and associated spectral distances of the Blob neighborhood, inter-Blob spectral distance, $\Delta d_{bs}$, and spectral distance parameter, $D_s$, are determined by Blob spectral data and information satisfying criteria of the above described particle spectral parameters, (i) pixel intensity, (ii) signal-to-noise ratio (S/N), (iii) image sharpness, and (v) spectral fingerprints relating to spectral emission patterns of individual particles. The procedure for establishing a Blob neighborhood starts by identifying a sufficiently sharp or focused Blob, $Blob_s$, having position coordinates $(x_s, y_s)$. During spectral imaging of sample 10, in a given gray level image of sample 10, there may be identified only one sharp or focused Blob, $Blob_s$, or, there may be identified a plurality of any number, S, of sharp or focused Blobs, for example, a first sharpest or most focused Blob, $Blob_s$, a second sharpest or most focused Blob, $Blob_{s+1}$, a third sharpest or most focused Blob, $Blob_{s+2}$, and so on until identifying the least sharpest or most focused Blob, $Blob_S$, of all the remaining detected $Blobs_b$, according to the above specific criteria for identifying a sharp or focused Blob, $Blob_s$.

Following identifying the sharpest or most focused Blob, $Blob_s$, having position coordinates $(x_s, y_s)$, in the gray level cube (spectral) image of sample 10, there is calculating a set of inter-Blob distances, $\Delta d_{bs}$, defined above in Step (2), sub-step (a), as the physical geometrical distance between each of all the identified Blobs, $Blob_b$, located at position coordinates $(x_b, y_b)$ in the i-th field of view, $FOV_i$, at the j-th differential imaging or focusing distance, $\Delta z_{ij}$, and the sharpest or most focused Blob, $Blob_s$, located at position coordinates $(x_s, y_s)$ in the same i-th field of view, $FOV_i$, at the same selected j-th differential imaging or focusing distance, $\Delta z_{ij}$.

Referring again to FIG. 2(A), for the purpose of description, each Blob neighborhood 60, 62, and 64, corresponds to a portion of a different single cube (spectral) plane image acquired for the same i-th field of view, $FOV_i$, 24, but, at a different j-th differential imaging or focusing distance, $\Delta z_{ij}$. For illustrating sub-step (b), of Step (5), it is assumed that only Blob neighborhood 60 appears in the cube (spectral) plane image acquired for the i-th field of view, $FOV_i$, 24, at differential imaging or focusing distance, $\Delta z_{i1}$. Furthermore, for illustrative purposes, it is assumed that the cube (spectral) plane image acquired for the i-th field of view, $FOV_i$, 24, at differential imaging or focusing distance, $\Delta z_{i1}$, includes $Blob_1$ 26, $Blob_2$ 28, $Blob_3$ 30, and $Blob_4$ 32, having position coordinates $(x_1, y_1)$, $(x_2, y_2)$, $(x_3, y_3)$, and $(x_4, y_4)$, respectively, and, also includes a plurality of other identified Blobs, $Blobs_b$ (not shown in FIG. 2(A)), having a corresponding plurality of position coordinates $(x_b, y_b)$, and, a plurality of non-Blob spectral features and/or artifacts (not shown in FIG. 2(A)) not satisfying criteria for being identified as a Blob, $Blob_b$, having a corresponding plurality of position coordinates (x, y).

Accordingly, in the cube (spectral) plane image acquired for the i-th field of view, $FOV_i$, 24, at differential imaging or focusing distance, $\Delta z_{i1}$, there is identifying a first sharpest or most focused $Blob_b$, referred to then as $Blob_s$, for example, $Blob_2$ 28, having position coordinates $(x_2, y_2)$. Then, there is calculating the inter-Blob distance between $Blob_1$ 26, having position coordinates $(x_1, y_1)$ and $Blob_2$ 28, indicated as $\Delta d_{12}$, calculating the inter-Blob distance between $Blob_3$ 30 having position coordinates $(x_3, y_3)$ and $Blob_2$ 28, indicated as $\Delta d_{32}$, calculating the inter-Blob distance between $Blob_4$ 32 having position coordinates $(x_4, y_4)$ and $Blob_2$ 28, indicated as $\Delta_{42}$, and calculating the inter-Blob distance, $\Delta d_{b2}$, between each of the remaining plurality of identified Blobs, $Blobs_b$ (not shown in FIG. 2(A)) having a corresponding plurality of position coordinates $(x_b, y_b)$.

Next, there is determining neighboring Blobs, where, hereinafter, each r-th neighboring Blob is referred to as $N_r$-$Blob_s$, for r=1 to any number, R, of neighboring Blobs, from all of the identified Blobs, $Blobs_b$, to be included and grouped in the Blob neighborhood associated with the sharpest or most focused Blob, $Blob_s$, by applying specific criteria to each of the inter-Blob distances, $\Delta d_{bs}$, between each of the identified Blobs, $Blobs_b$, and the sharpest or most focused Blob, $Blob_s$.

The criteria for determining a number of r-th neighboring Blobs, $N_r$-$Blob_s$, from all of the identified $Blobs_b$, are according to one of the following alternative logical comparative operations:

(1) $Blob_b$ having position coordinates $(x_b, y_b)$ is to be within a physical geometrical distance of no more than about three pixel diameters away from the sharpest or most focused Blob, $Blob_s$, having position coordinates $(x_s, y_s)$. This criterion is equivalently written as: inter-Blob distance, $\Delta d_{bs}$, is to be less than or equal to about $3D_{pixel}$, where $D_{pixel}$ is the pixel diameter, in order for $Blob_b$ to be identified and included as a neighboring Blob, $N_r$-$Blob_s$. Alternatively, (2) $Blob_b$ having position coordinates $(x_b, y_b)$ is to be within a physical geometrical distance of about two diameters of $Blob_s$ away from the sharpest or most focused Blob, $Blob_s$, having position coordinates $(x_s, y_s)$, and, $Blob_b$ is to have a similar spectral fingerprint pattern as the spectral fingerprint pattern of the sharpest or most focused Blob, $Blob_s$. This criterion is equivalently written as: inter-Blob distance, $\Delta d_{bs}$, is to be less than about $2D_{Blob-s}$, where $D_{Blob-s}$ is the diameter of $Blob_s$, and, $Blob_b$ is to have similar spectral fingerprint pattern as the spectral fingerprint pattern of the sharpest or most focused Blob, $Blob_s$, in order for $Blob_b$ to be identified and included as a neighboring Blob, $N_r$-$Blob_s$.

It is noted that the first alternative criterion, (1), features only a distance requirement, whereby an identified Blob, $Blob_b$, must be sufficiently close, for example, less than about three pixel diameters, to the sharpest or most focused Blob, $Blob_s$, in order for $Blob_b$ to be identified and included as a neighboring Blob, $N_r$-$Blob_s$, whereas, the second alternative criterion, (2), features a relatively less stringent distance requirement, whereby an identified Blob, $Blob_b$, must be sufficiently close, for example, less than about two Blob diameters, to the sharpest or most focused Blob, $Blob_s$, but, also features a spectral requirement, whereby $Blob_b$ is to have similar spectral fingerprint pattern as the spectral fingerprint pattern of the sharpest or most focused Blob, $Blob_s$, in order for $Blob_b$ to be identified and included as a neighboring Blob, $N_r\text{-}Blob_s$. Satisfying either of the two alternative criterion is indicative that an identified Blob, $Blob_b$, belongs in a Blob neighborhood initially established using the sharpest or most focused Blob, $Blob_s$, and that the spectral content and features, relating to the physicochemical properties, of $Blob_b$ are similar to those of the sharpest or most focused Blob, $Blob_s$, which serves as a very essential step for accurately classifying particle characteristics of particulate sample 10.

Referring again to FIG. 2(A), for example, an alternative criterion (1) or (2) is applied to each of the identified Blobs, $Blobs_b$, featuring a spectral fingerprint pattern, and featuring an inter-Blob distance, $\Delta d_{bs}$, between the identified Blob, $Blobs_b$, and the sharpest or most focused Blob, $Blob_2$ 28. Specifically, an alternative criterion (1) or (2) is applied to each of the identified Blobs, $Blob_1$ 26, $Blob_3$ 30, $Blob_4$ 32, and the remaining plurality of identified Blobs, $Blobs_b$, each featuring a spectral fingerprint pattern, and a previously calculated inter-Blob distance, $\Delta d_{12}$, $\Delta d_{32}$, $\Delta d_{42}$, and the plurality of $\Delta d_{b2}$, respectively. For example, and for illustrative purposes, it is assumed that each of the previously calculated inter-Blob distances $\Delta d_{12}$, $\Delta d_{32}$, and $\Delta d_{42}$, satisfies at least one of the alternative criteria (1) or (2), whereas, none of the previously calculated plurality of inter-Blob distances $\Delta d_{b2}$ satisfies at least one of the alternative criteria (1) or (2). Accordingly, $Blob_1$ 26, $Blob_3$ 30, and $Blob_4$ 32, having position coordinates $(x_1, y_1)$, $(x_3, y_3)$, and $(x_4, y_4)$, respectively, satisfy the requirement for being determined as neighboring Blobs, $N_r\text{-}Blob_s$, from all of the identified Blobs, $Blobs_b$, and are to be included and grouped in the Blob neighborhood associated with the first sharpest or most focused Blob, $Blob_2$ 28.

Following the grouping of neighboring Blobs, $N_r\text{-}Blob_s$, with respect to the first sharpest or most focused Blob, $Blob_s$, for example, $Blob_2$ 28, there is repeating the above procedure for the same cube (spectral) plane image acquired for the i-th field of view, and at the same j-th differential imaging or focusing distance $\Delta z_{ij}$ in $FOV_i$, for example, $FOV_i$ 24 at differential imaging or focusing distance, $\Delta z_{i1}$, for each of the successively sharpest or most focused Blobs, $Blob_{s+}$, $Blob_{s+2}$, $Blob_{s+3}$, . . . , $Blob_s$, having position coordinates $(x_{s+1}, y_{s+1})$, $(x_{s+2}, y_{s+2})$, $(x_{s+3}, y_{s+3})$, . . . , $(x_S, y_S)$, respectively, for determining additional Blob neighborhoods, where each additional Blob neighborhood is associated with a successively sharpest or most focused Blob, $Blob_{s+1}$, $Blob_{s+2}$, $Blob_{s+3}$, . . . , $Blob_S$, respectively, having position coordinates $(x_{s+1}, y_{s+1})$, $(x_{s+2}, y_{s+2})$, $(x_{s+3}, y_{s+3})$, . . . , $(x_S, y_S)$, respectively.

For illustrative purposes, for example, in FIG. 2(A), it is assumed that $Blob_1$ 26, $Blob_3$ 30, and $Blob_4$ 32, having position coordinates $(x_1, y_1)$, $(x_3, y_3)$, and $(x_4, y_4)$, respectively, are the only Blobs satisfying the requirement for being determined as neighboring Blobs, $N_r\text{-}Blob_s$, from all of the identified Blobs, $Blobs_b$, and are to be included and grouped in the Blob neighborhood associated with the sharpest or most focused Blob, $Blob_2$ 28. Accordingly, $Blob_1$ 26, $Blob_3$ 30, and $Blob_4$ 32, are hereinafter referred to as neighboring Blobs, $N_1\text{-}Blob_2$ 26, $N_2\text{-}Blob_2$ 30, and $N_3\text{-}Blob_2$ 32, and, are to be included and grouped in the Blob neighborhood associated with sharpest or most focused Blob, $Blob_2$ 28.

For illustrative purposes, for the cube (spectral) plane image of sample 10 acquired for the i-th field of view, $FOV_i$, for example, $FOV_i$ 24, at the j-th differential imaging or focusing distance, $\Delta z_{ij}$, for example, differential imaging or focusing distance, $\Delta z_{i1}$, it is assumed that only one Blob neighborhood, Blob neighborhood 60, satisfies the criteria of being a Blob neighborhood. Accordingly, there is constructing a 'focused' cube (spectral) plane image of sample 10, for the i-th field of view, $FOV_i$, for example, $FOV_i$ 24, at the j-th differential imaging or focusing distance, $\Delta z_{ij}$, for example, differential imaging or focusing distance, $\Delta z_{i1}$, from Blob neighborhood 60, featuring sharpest or most focused Blob, $Blob_2$ 28, and neighboring Blobs, $N_1\text{-}Blob_2$ 26, $N_2\text{-}Blob_2$ 30, and $N_3\text{-}Blob_2$ 32. This is illustrated in FIG. 2(B), as focused cube plane $image_{i1}$, 66, corresponding to the focused cube (spectral) image constructed from the cube (spectral) plane image acquired in the i-th field of view, $FOV_i$, at differential imaging or focusing distance, $\Delta z_{i1}$.

In sub-step (c), of Step (5), there is calculating a set of particle physicochemical and particle spectral parameters, relating to particle chemistry, particle morphology, and particle spectral fingerprints, for each identified Blob, $Blob_b$, in the i-th field of view, $FOV_i$, at the j-th differential imaging or focusing distance, $\Delta z_{ij}$, of the cube (spectral) plane image of sample 10 acquired in Step (4).

Morphological parameters relate to the size, area, shape, and central gravity position coordinates (x, y) of each identified Blob, $Blob_b$, which in turn, relate to particle characteristics in sample 10. The morphological parameters are calculated from spectral data and information obtained from the gray level cube (spectral) plane images of sample 10, followed by applying a high-pass filter to the spectral data and information of each identified $Blob_b$.

Spectral parameters relate to emission characteristics, for example, spectral fingerprints relating to spectral emission patterns featured in the emission spectra, of imaged particles in sample 10. The spectral parameters of each identified Blob, $Blob_b$, in each cube (spectral) plane image are calculated by applying a statistical algorithm to all the pixels constituting each $Blob_b$, for determining the quality of the spectral distances of the pixels, in general, and how close the pixels are to each other, in particular, in each identified $Blob_b$. The spectral parameters are evaluated from mean square error calculations.

In sub-step (d), of Step (5), there is calculating a focus-fusion factor parameter, $F_b$, from the set of physicochemical and spectral parameters previously calculated according to Step 5, sub-step (c), for each identified Blob, $Blob_b$, in the i-th field of view, $FOV_i$, at the j-th differential imaging or focusing distance, $\Delta z_{ij}$, of the cube (spectral) plane image of sample 10 acquired in Step (4), by using a formula based on applying fuzzy logic analysis:

$$F_b = \text{fuzzy logic function [(physicochemical parameters of } Blob_b\text{),}$$
$$\text{(spectral parameters of } Blob_b\text{)]},$$

where the physicochemical parameters of $Blob_b$ relate to particle chemistry and particle morphology, and the spectral parameters of $Blob_b$ relate to spectral fingerprints featured in spectral emission patterns of individual particles of sample 10.

For example, a corresponding focus-fusion factor parameter, $F_1$, $F_2$, $F_3$, $F_4$, and a plurality of $F_b$, is calculated for each of the identified Blobs, $Blob_1$ 26, $Blob_2$ 28, $Blob_3$ 30, $Blob_4$ 32, and the remaining plurality of identified Blobs, $Blobs_b$, for b=5 to B identified Blobs, respectively. The focus-fusion factor parameter, $F_b$, uniquely combines particle physicochemical and particle spectral information, to be used in a decision step for discriminating Blobs from each other, for example, involving identifying a number of high content Blobs from the total number of all identified Blobs, $Blobs_b$. This uniquely determined parameter enables achievement of high levels of accuracy and precision in detection and classification of the sample, in general, and of the featured particles, in particular.

In sub-step (e), of Step (5), there is selecting high content Blobs from all of the neighboring Blobs, $N_r$-$Blob_s$, of each Blob neighborhood grouped into a focused cube (spectral) plane $image_{ij}$ of sample 10, for the i-th field of view, $FOV_i$, at the j-th differential imaging or focusing distance, $\Delta z_{ij}$, according to previous Step 5, sub-step (b). Hereinafter, each c-th high content Blob in a given Blob neighborhood associated with a sharpest or most focused Blob, $Blob_s$, is referred to as $HC_c$-$Blob_s$, for c=1 to any number, C, of high content Blobs.

High content Blobs, $HC_c$-$Blob_s$, are selected according to decisions made by using above described spectral parameters (i) pixel intensity, (ii) signal-to-noise ratio (S/N), (iii) image sharpness, and (v) spectral fingerprints relating to spectral emission patterns of individual particles, and, the focus-fusion factor parameter, $F_b$, previously calculated in Step (5), sub-step (d), associated with each neighboring Blob, $N_r$-$Blob_s$. High content Blobs are to be used for constructing a 'fused' focused cube (spectral) image of sample 10, according to Step (7), below, for representing a highly accurate three-dimensional multi-layer image of a selected portion of sample 10, ultimately, providing useful image content relating to particle characteristics.

High content Blobs, $HC_c$-$Blob_s$, are selected as follows. In each Blob neighborhood, each neighboring Blob, $N_r$-$Blob_s$, is associated with position coordinates $(x_s+/-\delta x, y_s+/-\delta y)$, where the terms $(+/-\delta x)$ and $(+/-\delta y)$ represent small displacements from the position coordinates, $(x_s, y_s)$, of the sharpest or most focused Blob, $Blob_s$, used for generating that Blob neighborhood. The criteria for selecting a number of high content Blobs, $HC_c$-$Blob_s$, from all the neighboring Blobs, $N_r$-$Blob_s$, is according to the following two criteria:

1. The signal-to-noise ratio (S/N), associated with the imaging signal or spectrum corresponding to the summed or integrated intensities of the pixels in the gray level image representation of the high content Blob, $HC_c$-$Blob_s$, must be sufficiently high, for example, above a pre-determined signal-to-noise (S/N) threshold level, and, the high content Blob, $HC_c$-$Blob_s$, features at least one, preferably, more than one, spectral finger print relating to useful physicochemical information about sample 10, and
2. The focus-fusion factor parameter, $F_s$, for the high content Blob, $HC_c$-$Blob_s$, needs to be of an appropriate value.

An example of implementing this sub-step is illustrated in FIG. 2(B). From Step (5), sub-step (b), there was constructed a 'focused' cube (spectral) plane image of sample 10, for example, focused cube plane $image_{i1}$, 66, for the i-th field of view, $FOV_i$, for example, $FOV_i$ 24, at the j-th differential imaging or focusing distance, $\Delta z_{ij}$, for example, differential imaging or focusing distance, $\Delta z_{i1}$, from Blob neighborhood 60, featuring sharpest or most focused Blob, $Blob_2$ 28, and neighboring Blobs, $N_1$-$Blob_2$ 26, $N_2$-$Blob_2$ 30, and $N_3$-$Blob_2$ 32. Each of these neighborhood Blobs is subjected to the above criteria for being selected as a high content Blob, $HC_c$-$Blob_s$, following which remains only those Blobs satisfying the criteria. For illustrative purposes, as an example, it is assumed that in focused cube plane $image_{i1}$ 66, sharpest or most focused Blob, $Blob_2$ 28, and two neighboring Blobs, $N_1$-$Blob_2$ 26, and $N_2$-$Blob_2$ 30 (drawn as solid circles in focused cube plane $image_{i1}$ 66 in FIG. 2(B)), each satisfy the criteria for being selected as a high content Blob, $HC_c$-$Blob_s$, whereas, a single neighboring Blob, $N_3$-$Blob_2$ 32, (drawn as an 'x' in focused cube plane $image_{i1}$ 66 in FIG. 2(B)), fails to satisfy the criteria for being selected as a high content Blob, $HC_c$-$Blob_s$. Accordingly, in focused cube plane $image_{i1}$ 66, sharpest or most focused Blob, $Blob_2$ 28, and two neighboring Blobs, $N_1$-$Blob_2$ 26, and $N_2$-$Blob_2$ 30, are subsequently treated as high content Blobs, and are referred to as $HC_1$-$Blob_2$ 28, $HC_2$-$Blob_2$ 26, and $HC_3$-$Blob_2$ 30, respectively. These selected high content Blobs, $HC_c$-$Blob_s$, are used in constructing a 'fused' focused cube (spectral) image of sample 10, ultimately, providing useful image content relating to particle characteristics.

In sub-step (f), of Step (5), there is saving the above focused cube (spectral) plane image data in a focused cube (spectral) plane image database, for use in constructing a 'fused' focused cube (spectral) image of sample 10.

In Step (6), there is repeating Step (4) through Step (5) in the same field of view, $FOV_i$, for the selected range of the imaging distance defined along the z-axis between sample 10 and the light illumination source of imaging system 18. Accordingly, there is acquiring a plurality of cube (spectral) plane images of sample 10, in a corresponding plurality of selected i-th fields of view, $FOV_i$, where for each i-th field of view, $FOV_i$, there is imaging at a plurality of selected j-th differential imaging or focusing distances, $\Delta z_{ij}$, by focusing imaging system 18 by moving translation stage 20 in the z-direction an increment $\Delta z$, until receiving a sharp gray level image of sample 10. This corresponds to adjusting and setting imaging system 18 for spectral imaging sample 10 in a plurality of x-y planes of each of the plurality of i-th fields of view, $FOV_i$, for a plurality of selected differential imaging or focusing distances, $\Delta z_{ij}$. This step enables the acquisition of multi-layer, depth-dependent, spectral image data of sample 10.

Repetition of Step (4) through Step (5) is illustrated in FIGS. 2(A)–2(B). In FIG. 2(A), two additional Blob neighborhoods, Blob neighborhood 62 and Blob neighborhood 64 are shown. Blob neighborhood 62 features a sharpest or most focused Blob, for example, $Blob_9$ 42, and four neighboring Blobs, $N_1$-$Blob_9$ 34, $N_2$-$Blob_9$ 36, $N_3$-$Blob_9$ 38, and $N_4$-$Blob_9$ 40, and, Blob neighborhood 64 features a sharpest or most focused Blob, for example, $Blob_{13}$ 50, and four neighboring Blobs, $N_1$-$Blob_{13}$ 44, $N_2$-$Blob_{13}$ 46, $N_3$-$Blob_{13}$ 48, and $N_4$-$Blob_{13}$ 52, where each Blob has appropriately identified position coordinates (x, y).

Accordingly, there is constructing two additional 'focused' cube (spectral) plane images of sample 10, for the i-th field of view, $FOV_i$, for example, $FOV_i$ 24, at two additional j-th differential imaging or focusing distance, $\Delta z_{ij}$, for example, differential imaging or focusing distances, $\Delta z_{i2}$, and $\Delta z_{i3}$, from Blob neighborhood 62, and from Blob neighborhood 64, respectively. This is illustrated in FIG. 2(B), as focused cube plane $image_{i2}$ 68, and focused cube plane $image_{i3}$ 70.

In focused cube plane $image_{i2}$ 68, sharpest or most focused Blob, $Blob_9$ 42, and two neighboring Blobs, $N_1$-$Blob_9$ 34, and $N_2$-$Blob_9$ 36, are subsequently treated as high content Blobs, and are referred to as $HC_1$-$Blob_9$ 42, $HC_2$-$Blob_9$ 34, and $HC_3$-$Blob_9$ 36, respectively. In focused cube plane $image_{i3}$ 70, sharpest or most focused Blob, $Blob_{13}$ 50, and two neighboring Blobs, $N_1$-$Blob_{13}$ 44, and $N_2$-$Blob_{13}$ 48, are subsequently treated as high content Blobs, and are referred to as $HC_1$-$Blob_{13}$ 50, $HC_2$-$Blob_{13}$ 44, and $HC_3$-$Blob_{13}$ 48, respectively. These selected high content Blobs, $HC_c$-$Blob_s$, are subsequently also used, along with the high content Blobs, $HC_1$-$Blob_2$ 28, $HC_2$-$Blob_2$ 26, and $HC_3$-$Blob_2$ 30, which were selected for constructing focused cube plane $image_{i1}$ 66, for constructing a single 'fused' focused cube (spectral) image of sample 10, for example, fused focused cube (spectral) $image_i$ 72, shown in FIG. 2(C), for providing useful image content relating to particle characteristics. This procedure is a clear illustration of uniquely applying focus-fusion for multi-layer spectral imaging and analysis of particulate sample 10 featuring large layer or depth variations relative to changes in the imaging distance.

In Step (7), there is constructing a single 'fused' focused cube (spectral) image using the focused cube (spectral) plane image database of Step (5), sub-step (f), and using empirically determined spectral background parameters, $B_i$, for determining the spectral background area of the fused focused cube (spectral) image.

Of all the Blobs identified during acquiring and analyzing images of sample 10, preferably, only the high content Blobs, $HC_c$-$Blob_s$, selected from the focused cube (spectral) plane image database, are featured in each fused focused cube (spectral) image.

In sub-step (a) of Step (7), there is determining the spectral background area of the fused focused cube (spectral) image. For each fused focused cube (spectral) $image_i$, to be constructed from the plurality of focused cube (spectral) plane $images_{ij}$, the spectral background area, corresponding to background pixels (voxels) not associated with any detected or identified targets or Blobs in the focused cube (spectral) $images_{ij}$ of sample 10, is determined from the spectral background area of the sharpest focused cube (spectral) plane $image_{ij}$, acquired for the i-th field of view, $FOV_i$, at differential imaging or focusing distances, $\Delta z_{ij}$, featuring the highest levels of spatial and frequency content.

Spectral background area parameters, $B_i$, are determined from measurements of sharpness of each of the plurality of focused cube (spectral) plane $images_{ij}$, acquired for the i-th field of view, $FOV_i$, at differential imaging or focusing distances, $\Delta z_{ij}$. Specifically, these sharpness measurements are used for calculating spectral background area parameters, $B_i$, based on a factor of the local differences in intensities and positions of all the background pixels, in the spectral background area, not associated with any detected or identified targets or Blobs in the focused cube (spectral) $images_{ij}$ of sample 10.

Construction of an exemplary fused focused cube (spectral) image from the plurality of focused cube (spectral) plane $images_{ij}$, is illustrated in FIGS. 2(B)–(C). High content Blobs, $HC_1$-$Blob_2$ 28, $HC_2$-$Blob_2$ 26, and $HC_3$-$Blob_2$ 30, obtained from focused cube plane $image_{i1}$ 66, and, high content Blobs, $HC_1$-$Blob_9$ 42, $HC_2$-$Blob_9$ 34, and $HC_3$-$Blob_9$ 36, obtained from focused cube plane $image_{i2}$ 68, and, high content Blobs, $HC_1$-$Blob_{13}$ 50, $HC_2$-$Blob_{13}$ 44, and $HC_3$-$Blob_{13}$ 48, obtained from focused cube plane $image_{i3}$ 70, are selected from the focused cube (spectral) plane image database of Step (5), sub-step (f), for constructing fused focused cube (spectral) $image_i$ 72, shown in FIG. 2(C), for providing useful image content relating to particle characteristics. In exemplary fused focused cube (spectral) $image_i$ 72, spectral background area 74 is obtained, for example, from spectral background pixels of focused cube (spectral) plane $image_{i2}$, by performing sharpness measurements on the focused cube (spectral) plane $images_{ij}$ illustrated in FIG. 2(B).

Also shown in FIG. 2(C), is exemplary particle emission spectrum 76, associated with fused focused cube (spectral) $image_i$ 72, illustrating exemplary spectral fingerprints 78, relating to physicochemical characteristics of sample 10, which are used throughout the above described steps of implementing the method for in-situ focus-fusion multi-layer spectral imaging and analysis of particulate sample 10.

In sub-step (b), of Step (7), there is saving the above fused focused cube (spectral) image data in a fused focused cube (spectral) image database, for use in image analysis algorithms (Step (9)).

In Step (8), there is acquiring and constructing additional fused focused cube (spectral) images of sample 10 in other fields of view, $FOV_i$, for a plurality of differential imaging or focusing distances, $\Delta z_{ij}$, by repeating Step (3) through Step (7), until the selected sample viewing/imaging range is imaged. This is, in part, accomplished by programmed movement of translation stage 20 to other fields of view over sample 10, and in each field of view, incremental movement of translation stage 20 to different selected differential imaging or focusing distances, $\Delta z_{ij}$.

In Step (9), there is applying one or more image analysis algorithms to the database of fused focused cube (spectral) images. The plurality of fused focused cube (spectral) images are analyzed for spectral fingerprints, whereby spectral data is related to physicochemical characteristics of sample 10.

In sub-step (a), of Step (9), there is using detection, classification, and/or decision algorithms for image analysis of the fused focused cube (spectral) image data. Examples of specific detection, classification, and/or decision algorithms suitable for image analysis in the method of the present invention are fully described in U.S. Pat. No. 5,880,830, issued to Schechter, and in U.S. Pat. No. 6,091,843, and references cited therein, which are incorporated by reference for all purposes as if fully set forth herein. Calibration data of standard samples with known physicochemical and spectral imaging characteristics are used as part of the image analysis. In the present invention, image analysis is based on uniquely combining physicochemical data, such as morphological and chemical composition data, with multi-layer spectral imaging data of particulate sample 10. This unique combination enables achievement of high levels of accuracy and precision in detection and classification of sample 10, in general, and of the featured particles, in particular.

In sub-step (b), of Step (9), there is generating a statistical analysis report of the image analysis results.

In Step (10), there is repeating Step (3) through Step (9) for each pre-determined time interval, $\Delta t$. Accordingly, following each pre-determined time interval, $\Delta t$, there is generating a statistical analysis report describing time variation of the physicochemical and spectral imaging characteristics of particulate sample 10. This step further enables achievement of high levels of accuracy and precision in detection and classification of particulate sample 10.

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for in-situ focus-fusion multi-layer spectral imaging and analysis of a particulate sample, particles of the particulate sample exhibiting layer or depth dependent features and characteristics, the method comprising the steps of:

(a) preparing the sample for the in-situ focus-fusion multi-layer spectral imaging and analysis;

(b) providing a spectroscopic imaging system, including a light illumination source and a sample holder moveable by a three dimensional translation stage, for in-situ spectral imaging of the sample;

(c) selecting and defining imaging scenario parameters for acquiring and analyzing in-situ spectral images of the sample, said imaging scenario parameters are particle physicochemical information and characteristics relating to particle chemical composition and particle morphology, and, particle spectral information and characteristics relating to pixel energy level or intensity, I(p), signal-to-noise ratio, (S/N), image sharpness, spectral distances, and spectral fingerprints relating to spectral emission patterns of the particles of the sample, each said spectral emission pattern featuring emission intensity as a function of wavelength of light emitted by the sample;

(d) adjusting and setting said spectroscopic imaging system for said in-situ spectral imaging of the sample at a selected i-th field of view, $FOV_i$, having central (x, y) position coordinates relative to said translation stage;

(e) acquiring a cube (spectral) plane image of the sample in said selected i-th field of view, $FOV_i$, at a selected j-th differential imaging/focusing distance, $\Delta z_{ij}$, in a selected range of imaging distance defined along z-direction between the sample and said light illumination source of said spectroscopic imaging system, by focusing said imaging system in said z-direction until receiving a sharp gray level image of the sample;

(f) constructing and analyzing a focused cube (spectral) plane image$_{ij}$, of the sample for said selected i-th field of view, $FOV_i$, at said selected j-th differential imaging/focusing distance, $\Delta z_{ij}$, from said acquired cube (spectral) plane image of the sample, whereby said constructing and analyzing features identifying targets in said sharp gray level image of the sample by using said selected and said defined particle physicochemical imaging scenario parameters and said selected and said defined particle spectral imaging scenario parameters;

(g) repeating step (e) and step (f) in said selected i-th field of view, $FOV_i$, for a plurality of said selected j-th differential imaging/focusing distances, $\Delta z_{ij}$, in said selected range of imaging distance, for forming a plurality of said focused cube (spectral) plane images$_{ij}$ of the sample for said selected i-th field of view, $FOV_i$;

(h) constructing a fused focused cube (spectral) image$_i$, for said selected i-th field of view, $FOV_i$, using a plurality of said identified targets having high content selected from said plurality of said focused cube (spectral) plane images$_{ij}$, and, using spectral background parameters, $B_i$, empirically determined from said plurality of said focused cube (spectral) plane images$_{ij}$;

(i) acquiring and constructing a plurality of said fused focused cube (spectral) images$_i$ of the sample in other said selected i-th fields of view, $FOV_i$, having corresponding said central (x, y) position coordinates relative to said translation stage, for a plurality of said selected j-th differential imaging/focusing distances, $\Delta z_{ij}$, by repeating step (d) through step (h), until selected sample viewing/imaging range is imaged and analyzed;

(j) applying at least one image analysis algorithm to data of said plurality of said fused focused cube (spectral) images$_i$ for identifying spectral fingerprints relating to physicochemical characterization of the sample; and (k) repeating step (d) through step (j) following each predetermined time interval, $\Delta t$, over a period of time spanning a multiple of said pre-determined time interval, $\Delta t$, for generating a statistical analysis report describing time variation of physicochemical and spectral imaging characteristics of the particulate sample.

2. The method of claim 1, wherein the particulate sample is selected from the group consisting of a pure powder, a powder mixture, a medicinal powder featuring at least one active ingredient and at least one inactive ingredient, a frozen suspension of a powder, and a biological specimen, featuring a three dimensional topography whereby variations of the layer or depth dependent features and characteristics of the sample in said z-direction along height of the sample are relatively large compared to each said selected j-th differential imaging/focusing distance, $\Delta z_{ij}$, in said selected range of said imaging distance.

3. The method of claim 1, wherein during said in-situ spectral imaging of the sample, the sample is at conditions selected from the group consisting of exposed to ambient conditions without controlled environmental containment and contained in a controlled environment.

4. The method of claim 1, wherein step (f) said particle physicochemical imaging scenario parameters are selected from the group consisting of chemistry of the particles of the sample, size of the particles of the sample, and, shape of the particles of the sample.

5. The method of claim 1, wherein step (f) said spectral distances of said particle spectral imaging scenario parameters are physical geometrical distances separating selected cube (spectral) sets of groups or clusters of individual pixels in a said sharp gray level image representation of the sample with each said pixel having location or position coordinates, (x, y), and said pixel energy level or intensity, I(p), in said sharp gray level image of the sample.

6. The method of claim 1, whereby step (f) includes the steps of:

(i) identifying Blobs$_b$ in said acquired cube (spectral) plane image of the sample, each said Blob$_b$ is made up of a cube (spectral) set of groups or clusters of individual pixels in a said sharp gray level image representation of the sample with each said pixel having location or position coordinates, (x, y), and said pixel energy level or intensity, I(p), in said sharp gray level image of the sample, whereby each said Blob$_b$ having position coordinates ($x_b$, $y_b$) in said sharp gray level image of the sample features a sufficiently high fraction of all said pixels in said group or cluster of said pixels constituting said Blob$_b$ having said pixels each having said pixel energy level or intensity, I(p), above a pre-determined threshold pixel energy level or intensity, $I_T(p)$, and whereby each said Blob$_b$ features a sufficiently high said signal-to-noise ratio, (S/N), associated with an imaging signal corresponding to summed or integrated intensities of all said pixels of said Blob$_b$; and (ii) grouping a plurality of selected neighboring identified Blobs$_b$ from all said identified Blobs$_b$ into at least one Blob neighborhood for said acquired cube (spectral) plane image of the sample, for forming said focused cube (spectral) plane image$_{ij}$ of the sample featuring a number of said plurality of said selected neighboring identified Blobs$_b$ as $N_r$-Blobs$_s$.

7. The method of claim 6, wherein step (ii) forming each said Blob neighborhood comprises the steps of:

(1) identifying a sharpest or most focused said Blob$_b$ in said acquired cube (spectral) plane image of the sample, said sharpest or most focused said $Blob_b$ denoted as $Blob_s$ having position coordinates $(x_s, y_s)$;

(2) determining a first type of said spectral distances as Blob neighborhood spectral distance parameter, $D_s$, whereby said Blob neighborhood spectral distance parameter, $D_s$, is a physical geometrical distance encompassing said number of said selected neighboring $N_r$-$Blobs_s$ in each said Blob neighborhood associated with said sharpest or most focused $Blob_s$;

(3) calculating a second type of said spectral distances as inter-Blob distance, $\Delta d_{bs}$, for each of all said identified $Blobs_b$, whereby each said inter-Blob distance $\Delta d_{bs}$, is physical geometrical distance between each of all said identified $Blobs_b$ located at said position coordinates $(x_b, y_b)$ and said sharpest or most focused $Blob_s$ located at said position coordinates $(x_s, y_s)$ in same said selected i-th field of view, $FOV_i$, at same said selected j-th differential imaging/focusing distance, $\Delta z_{ij}$; and (4) determining said number of said selected neighboring $N_r$-$Blobs_s$ from all said identified $Blobs_b$ for said grouping into said Blob neighborhood associated with said sharpest or most focused $Blob_s$, by applying specific alternative criteria of logical comparative operations to each said inter-Blob distance, $\Delta d_{bs}$, between each said identified $Blob_b$ and said sharpest or most focused $Blob_s$, thereby forming each said Blob neighborhood.

8. The method of claim 7, whereby said specific alternative criteria of logical comparative operations are selected from the group consisting of a first specific alternative criterion and a second specific alternative criterion, whereby said first specific alternative criterion is where said identified $Blob_b$ having said position coordinates $(x_b, y_b)$ has said inter-Blob distance, $\Delta d_{bs}$, less than or equal to about $3D_{pixel}$, where said $D_{pixel}$ is a pixel diameter, and, whereby said second specific alternative criterion is where said identified $Blob_b$ having said position coordinates $(x_b, y_b)$ has said inter-Blob distance, $\Delta d_{bs}$, less than about $2D_{Blob-s}$, where said $D_{Blob-s}$ is diameter of said $Blob_s$, and, said identified $Blob_b$ has similar said spectral fingerprints as said spectral fingerprints of said sharpest or most focused $Blob_s$.

9. The method of claim 8, whereby following said grouping of said number of selected neighboring $N_r$-$Blob_s$ with respect to first said sharpest or most focused $Blob_s$, there is repeating step (1) through step (4) for same said acquired cube (spectral) plane image in same said selected i-th field of view, $FOV_i$, at same said j-th differential imaging/focusing distance $\Delta z_{ij}$ for each successively said sharpest or most focused $Blob_{s+1}$, $Blob_{s+2}$, $Blob_{s+3}$, . . . , $Blob_S$, having said position coordinates $(x_{s+1}, y_{s+1})$, $(x_{s+2}, y_{s+2})$, $(x_{s+3}, y_{s+3})$, . . . , $(x_S, y_S)$, respectively, for forming additional said Blob neighborhoods each associated with a said successively sharpest or most focused $Blob_{s+1}$, $Blob_{s+2}$, $Blob_{s+3}$, . . . , $Blob_S$, respectively, for a plurality of S said successively sharpest or most focused $Blob_s$, in same said acquired cube (spectral) plane image.

10. The method of claim 6, whereby step (f) further includes the steps of:

(iii) calculating a set of said particle physicochemical and said particle spectral imaging scenario parameters for each said identified $Blob_b$ of said acquired cube (spectral) plane image of the sample;

(iv) calculating a focus-fusion factor parameter, $F_b$, from said set of particle physicochemical and said particle spectral imaging scenario parameters of step (iii) for each said identified $Blob_b$ of said cube (spectral) plane image of the sample by using a formula based on applying fuzzy logic analysis, whereby said $F_b$ is evaluated from a fuzzy logic function of said particle physicochemical parameters of said $Blob_b$ and of said particle spectral parameters of said $Blob_b$; and (v) selecting at least one high content $Blob_b$ as $HC_c$-$Blob_s$ from said number of said selected neighboring $N_r$-$Blobs_s$ of each said Blob neighborhood of said focused cube (spectral) plane $image_{ij}$ of the sample, by applying specific criteria to each said selected neighboring $N_r$-$Blob_s$ of each said Blob neighborhood.

11. The method of claim 10, whereby said specific criteria for selecting said at least one high content $HC_c$-$Blob_s$, from said number of said selected neighboring $N_r$-$Blobs_s$, of each said Blob neighborhood include a first criterion whereby said signal-to-noise ratio (S/N) associated with said imaging signal corresponding to summed or integrated intensities of said pixels in said gray level image representation of a said selected neighboring $N_r$-$Blob_s$ is sufficiently above a predetermined signal-to-noise (S/N) threshold level, and, said selected neighboring $N_r$-$Blob_s$ features at least one said spectral fingerprint relating to said particle physicochemical information and characteristics of the sample, and, a second criterion whereby said focus-fusion factor parameter, $F_s$, of said selected neighboring $N_r$-$Blob_s$ is of an appropriate value.

12. The method of claim 10, whereby a plurality of said high content $HC_c$-$Blobs_s$ is used as said plurality of said targets having high content for performing step (h) for said constructing said fused focused cube (spectral) $image_i$ for said selected i-th field of view, $FOV_i$.

13. The method of claim 1, whereby in step (h) said spectral background parameters, $B_i$, are used for determining spectral background area of said fused focused cube (spectral) $image_i$ for said selected i-th field of view, $FOV_i$.

14. The method of claim 13, whereby said spectral background parameters, $B_i$, are determined from spectral background area of sharpest said focused cube (spectral) plane $image_{ij}$ featuring highest levels of spatial and frequency imaging content acquired for said selected i-th field of view, $FOV_i$, at said plurality of said j-th differential imaging/focusing distances, $\Delta z_{ij}$.

15. The method of claim 13, whereby said spectral background parameters, $B_i$, are determined from spectral background area of sharpest said focused cube (spectral) plane $image_{ij}$ acquired for said selected i-th field of view, $FOV_i$, at said plurality of said j-th differential imaging/focusing distances, $\Delta z_{ij}$, based on a factor of local differences in said pixel energy levels or intensities, I(p), and pixel positions of all pixels in said spectral background area of said sharpest focused cube (spectral) $image_{ij}$, whereby said pixels are not associated with a said identified target in said sharpest focused cube (spectral) $image_{ij}$ of the sample.

16. The method of claim 1, whereby step (f) further includes the steps of:

(iii) calculating a set of said particle physicochemical and said particle spectral imaging scenario parameters for each said identified target of said acquired cube (spectral) plane image of the sample;

(iv) calculating a focus-fusion factor parameter, $F_b$, from said set of particle physicochemical and said particle spectral imaging scenario parameters of step (iii) for each said identified target of said cube (spectral) plane image of the sample by using a formula based on applying fuzzy logic analysis, whereby said $F_b$ is evaluated from a fuzzy logic function of said particle physicochemical parameters of said identified target and of said particle spectral parameters of said identified target; and (v) selecting at least one said high content target from a number of neighboring identified targets of a target neighborhood of said focused cube (spectral) plane image$_{ij}$ of the sample, by applying specific criteria to each said neighboring identified target of each said target neighborhood.

17. The method of claim 16, whereby said specific criteria for selecting said at least one high content target from said number of said neighboring identified targets of each said target neighborhood include a first criterion whereby said signal-to-noise ratio (S/N) associated with said imaging signal corresponding to summed or integrated intensities of said pixels in said gray level image representation of a said neighboring identified target is sufficiently above a predetermined signal-to-noise (S/N) threshold level, and, said neighboring identified target features at least one said spectral fingerprint relating to said particle physicochemical information and characteristics of the sample, and, a second criterion whereby said focus-fusion factor parameter, $F_s$, of said neighboring identified target is of an appropriate value.

18. A method for spectral imaging and analyzing a particulate sample, particles of the particulate sample exhibiting layer or depth dependent features and characteristics, the method comprising the steps of:

(a) selecting and defining imaging scenario parameters for acquiring and analyzing in-situ spectral images of the sample, said imaging scenario parameters are particle physicochemical information and characteristics relating to particle chemical composition and particle morphology, and, particle spectral information and characteristics relating to pixel energy level or intensity, I(p), signal-to-noise ratio, (S/N), image sharpness, spectral distances, and spectral fingerprints relating to spectral emission patterns of the particles of the sample, each said spectral emission pattern featuring emission intensity as a function of wavelength of light emitted by the sample;

(b) acquiring a cube (spectral) plane image of the sample having central position (x,y) coordinates in a selected field of view, at a selected differential imaging/focusing distance in a selected range of imaging distance defined along z-direction between the sample and a light illumination source of an imaging device, by focusing said imaging device in said z-direction until receiving a sharp gray level image of the sample;

(c) constructing and analyzing a focused cube (spectral) plane image of the sample for said selected field of view at said selected differential imaging/focusing distance, from said acquired cube (spectral) plane image of the sample, whereby said constructing and analyzing features identifying targets in said sharp gray level image of the sample by using said selected and said defined particle physicochemical imaging scenario parameters and said selected and said defined particle spectral imaging scenario parameters;

(d) repeating step (b) and step (c) in said selected field of view for a plurality of said selected differential imaging/focusing distances in said selected range of imaging distance, for forming a plurality of said focused cube (spectral) plane images of the sample for said selected field of view;

(e) constructing a fused focused cube (spectral) image for said selected field of view using a plurality of said identified targets having high content selected from said plurality of said focused cube (spectral) plane images and using spectral background parameters, B, empirically determined from said plurality of said focused cube (spectral) plane images;

(f) acquiring and constructing a plurality of said fused focused cube (spectral) images of the sample in other said selected fields of view having corresponding said central (x, y) position coordinates, for a plurality of said selected differential imaging/focusing distances by repeating step (b) through step (e), until selected sample viewing/imaging range is imaged and analyzed;

(g) applying at least one image analysis algorithm to data of said plurality of said fused focused cube (spectral) images for identifying spectral fingerprints relating to physicochemical characterization of the sample; and (h) repeating step (b) through step (g) following each pre-determined time interval, $\Delta t$, over a period of time spanning a multiple of said predetermined time interval, $\Delta t$, for generating a statistical analysis report describing time variation of physicochemical and spectral imaging characteristics of the particulate sample.

19. The method of claim 18, wherein the particulate sample is selected from the group consisting of a pure powder, a powder mixture, a medicinal powder featuring at least one active ingredient and at least one inactive ingredient, a frozen suspension of a powder, and a biological specimen, featuring a three dimensional topography whereby variations of the layer or depth dependent features and characteristics of the sample in said z-direction along height of the sample are relatively large compared to each said selected differential imaging/focusing distance in said selected range of said imaging distance.

20. The method of claim 18, wherein during said in-situ spectral imaging of the sample, the sample is at conditions selected from the group consisting of exposed to ambient conditions without controlled environmental containment and contained in a controlled environment.

21. The method of claim 18, wherein step (c) said particle physicochemical imaging scenario parameters are selected from the group consisting of chemistry of the particles of the sample, size of the particles of the sample, and, shape of the particles of the sample.

22. The method of claim 18, wherein step (c) said spectral distances of said particle spectral imaging scenario parameters are physical geometrical distances separating selected cube (spectral) sets of groups or clusters of individual pixels in a said sharp gray level image representation of the sample with each said pixel having location or position coordinates, (x, y), and said pixel energy level or intensity, I(p), in said sharp gray level image of the sample.

23. The method of claim 18, whereby step (c) includes the steps of:

(i) identifying Blobs in said acquired cube (spectral) plane image of the sample, each said Blob is made up of a cube (spectral) set of groups or clusters of individual pixels in a said sharp gray level image representation of the sample with each said pixel having location or position coordinates, (x, y), and said pixel energy level or intensity, I(p), in said sharp gray level image of the sample, whereby each said Blob having position coordinates ($x_b$, $y_b$) in said sharp gray level image of the sample features a sufficiently high fraction of all said pixels in said group or cluster of said pixels constituting said Blob having said pixels each having said pixel energy level or intensity, I(p), above a pre-determined threshold pixel energy level or intensity, $I_t(p)$, and whereby each said Blob features a sufficiently high said signal-to-noise ratio, (S/N), associated with an imaging signal corresponding to summed or integrated intensities of all said pixels of said Blob; and (ii) grouping a plurality of selected neighboring identified Blobs from all said identified Blobs into at least one Blob neighborhood for said acquired cube (spectral) plane image of the sample, for forming said focused cube (spectral) plane image of the sample featuring a number of said plurality of said selected neighboring Blobs.

24. The method of claim 23, wherein step (ii) forming each said Blob neighborhood comprises the steps of:

(1) identifying a sharpest or most focused said Blob in said acquired cube (spectral) plane image of the sample, said sharpest or most focused Blob having position coordinates $(x_s, y_s)$;

(2) determining a first type of said spectral distances as Blob neighborhood spectral distance parameter being a physical geometrical distance encompassing said number of said selected neighboring Blobs in each said Blob neighborhood associated with said sharpest or most focused Blob;

(3) calculating a second type of said spectral distances as inter-Blob distance for each of all said identified Blobs, each said inter-Blob distance is physical geometrical distance between each of all said identified Blobs located at said position coordinates $(x_b, y_b)$ and said sharpest or most focused Blob located at said position coordinates $(x_s, y_s)$ in same said selected field of view at same said selected differential imaging/focusing distance; and (4) determining said number of said selected neighboring Blobs from all said identified Blobs for said grouping into said Blob neighborhood associated with said sharpest or most focused Blob, by applying specific alternative criteria of logical comparative operations to each said inter-Blob distance between each said identified Blob and said sharpest or most focused Blob, thereby forming each said Blob neighborhood.

25. The method of claim 24, whereby said specific alternative criteria of logical comparative operations are selected from the group consisting of a first specific alternative criterion and a second specific alternative criterion, whereby said first specific alternative criterion is where said identified Blob having said position coordinates $(x_b, y_b)$ has said inter-Blob distance less than or equal to about $3D_{pixel}$, where said $D_{pixel}$ is a pixel diameter, and, whereby said second specific alternative criterion is where said identified Blob having said position coordinates $(x_b, y_b)$ has said inter-Blob distance less than about $2D_{Blob-s}$, where said $D_{Blob-s}$ is diameter of said Blob, and, said identified Blob has similar said spectral fingerprints as said spectral fingerprints of said sharpest or most focused Blob.

26. The method of claim 25, whereby following said grouping of said number of selected neighboring Blobs with respect to first said sharpest or most focused Blob, there is repeating step (1) through step (4) for same said acquired cube (spectral) plane image in same said selected field of view at same said differential imaging/focusing distance for each successively said sharpest or most focused Blob having corresponding said position coordinates $(x_s, y_s)$, for forming additional said Blob neighborhoods each associated with a said successively sharpest or most focused Blob for a plurality of said successively sharpest or most focused Blobs in same said acquired cube (spectral) plane image.

27. The method of claim 23, whereby step (c) further includes the steps of:

(iii) calculating a set of said particle physicochemical and said particle spectral imaging scenario parameters for each said identified Blob of said acquired cube (spectral) plane image of the sample;

(iv) calculating a focus-fusion factor parameter, $F_b$, from said set of particle physicochemical and said particle spectral imaging scenario parameters of step (iii) for each said identified Blob of said cube (spectral) plane image of the sample by using a formula based on applying fuzzy logic analysis, whereby said $F_b$ is evaluated from a fuzzy logic function of said particle physicochemical parameters of said Blob and of said particle spectral parameters of said Blob; and (v) selecting at least one high content Blob from said number of said selected neighboring Blobs of each said Blob neighborhood of said focused cube (spectral) plane image of the sample, by applying specific criteria to each said selected neighboring Blob of each said Blob neighborhood.

28. The method of claim 27, whereby said specific criteria for selecting said at least one high content Blob from said number of said selected neighboring Blobs of each said Blob neighborhood include a first criterion whereby said signal-to-noise ratio (S/N) associated with said imaging signal corresponding to summed or integrated intensities of said pixels in said gray level image representation of a said selected neighboring Blob is sufficiently above a predetermined signal-to-noise (S/N) threshold level, and, said selected neighboring Blob features at least one said spectral fingerprint relating to said particle physicochemical information and characteristics of the sample, and, a second criterion whereby said focus-fusion factor parameter, $F_s$, of said selected neighboring Blob is of an appropriate value.

29. The method of claim 27, whereby a plurality of said high content Blobs is used as said plurality of said targets having high content for performing step (f) for said constructing said fused focused cube (spectral) image for said selected field of view.

30. The method of claim 18, whereby in step (f) said spectral background parameters, B, are used for determining spectral background area of said fused focused cube (spectral) image for said selected field of view.

31. The method of claim 30, whereby said spectral background parameters, B, are determined from spectral background area of sharpest said focused cube (spectral) plane image featuring highest levels of spatial and frequency imaging content acquired for said selected field of view at said plurality of said differential imaging/focusing distances.

32. The method of claim 30, whereby said spectral background parameters, B, are determined from spectral background area of sharpest said focused cube (spectral) plane image acquired for said selected field of view at said plurality of said differential imaging/focusing distances, based on a factor of local differences in said pixel energy levels or intensities, I(p), and pixel positions of all pixels in said spectral background area of said sharpest focused cube (spectral) image, whereby said pixels are not associated with a said identified target in said sharpest focused cube (spectral) image of the sample.

33. The method of claim 18, whereby step (c) further includes the steps of:

(iii) calculating a set of said particle physicochemical and said particle spectral imaging scenario parameters for each said identified target of said acquired cube (spectral) plane image of the sample;

(iv) calculating a focus-fusion factor parameter, $F_b$, from said set of particle physicochemical and said particle spectral imaging scenario parameters of step (iii) for each said identified target of said cube (spectral) plane image of the sample by using a formula based on applying fuzzy logic analysis, whereby said $F_b$ is evaluated from a fuzzy logic function of said particle physicochemical parameters of said identified target and of said particle spectral parameters of said identified target; and (v) selecting at least one said high content target from a number of neighboring identified targets of a target neighborhood of said focused cube (spectral) plane image of the sample, by applying specific criteria to each said neighboring identified target of each said target neighborhood.

34. The method of claim 33, whereby said specific criteria for selecting said at least one high content target from said number of said neighboring identified targets of each said target neighborhood include a first criterion whereby said signal-to-noise ratio (S/N) associated with said imaging signal corresponding to summed or integrated intensities of said pixels in said gray level image representation of a said neighboring identified target is sufficiently above a predetermined signal-to-noise (S/N) threshold level, and, said neighboring identified target features at least one said spectral fingerprint relating to said particle physicochemical information and characteristics of the sample, and, a second criterion whereby said focus-fusion factor parameter, $F_s$, of said neighboring identified target is of an appropriate value.

35. A method for spectral imaging and analyzing a particulate sample, particles of the particulate sample exhibiting layer or depth dependent features and characteristics, the method comprising the steps of:

(a) selecting and defining imaging scenario parameters for acquiring and analyzing in-situ spectral images of the sample, said imaging scenario parameters are particle physicochemical information and characteristics relating to particle chemical composition and particle morphology, and, particle spectral information and characteristics relating to pixel energy level or intensity, I(p), signal-to-noise ratio, (S/N), image sharpness, spectral distances, and spectral fingerprints relating to spectral emission patterns of the particles of the sample, each said spectral emission pattern featuring emission intensity as a function of wavelength of light emitted by the sample;

(b) sequentially acquiring a plurality of cube (spectral) plane images of the sample in a corresponding plurality of sequentially selected fields of view for a plurality of selected differential imaging/focusing distances in a selected range of imaging distance defined between the sample and a light illumination source of an imaging device, by sequentially focusing said imaging device along said imaging distance for sequentially receiving a plurality of sharp gray level images of the sample;

(c) constructing and analyzing a plurality of focused cube (spectral) plane images of the sample for said plurality of sequentially selected fields of view at said plurality of selected differential imaging/focusing distances, from said plurality of sequentially acquired cube (spectral) plane images of the sample, whereby said constructing and analyzing features identifying targets in each said sharp gray level image of the sample by using said selected and said defined particle physicochemical imaging scenario parameters and said selected and said defined particle spectral imaging scenario parameters;

(d) constructing a plurality of fused focused cube (spectral) images for said plurality of sequentially selected fields of view at said plurality of selected differential imaging/focusing distances, using a plurality of said identified targets having high content selected from said plurality of said focused cube (spectral) plane images and using spectral background parameters, B, empirically determined from said plurality of said focused cube (spectral) plane images; and (e) applying at least one image analysis algorithm to data of said plurality of said fused focused cube (spectral) images for identifying spectral fingerprints relating to physicochemical characterization of the sample.

36. The method of claim 35, wherein the particulate sample is selected from the group consisting of a pure powder, a powder mixture, a medicinal powder featuring at least one active ingredient and at least one inactive ingredient, a frozen suspension of a powder, and a biological specimen, featuring a three dimensional topography whereby variations of the layer or depth dependent features and characteristics of the sample along height of the sample are relatively large compared to each said selected differential imaging/focusing distance in said selected range of said imaging distance.

37. The method of claim 35, wherein during said in-situ spectral imaging of the sample, the sample is at conditions selected from the group consisting of exposed to ambient conditions without controlled environmental containment and contained in a controlled environment.

38. The method of claim 35, whereby said particle physicochemical imaging scenario parameters are selected from the group consisting of chemistry of the particles of the sample, size of the particles of the sample, and, shape of the particles of the sample.

* * * * *